United States Patent
Fukushima et al.

(10) Patent No.: US 12,037,530 B2
(45) Date of Patent: Jul. 16, 2024

(54) COMPOUND AND LIQUID CRYSTAL COMPOSITION

(71) Applicant: FUJIFILM Corporation, Tokyo (JP)

(72) Inventors: Yuki Fukushima, Minamiashigara (JP); Keisuke Kodama, Minamiashigara (JP); Shunya Katoh, Minamiashigara (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 17/889,523

(22) Filed: Aug. 17, 2022

(65) Prior Publication Data

US 2023/0002679 A1   Jan. 5, 2023

Related U.S. Application Data

(63) Continuation of application No. PCT/JP2021/005259, filed on Feb. 12, 2021.

(30) Foreign Application Priority Data

Feb. 18, 2020 (JP) ................................. 2020-024935

(51) Int. Cl.
*G02F 1/1333* (2006.01)
*C09K 19/16* (2006.01)
*C09K 19/20* (2006.01)

(52) U.S. Cl.
CPC .......... *C09K 19/2007* (2013.01); *C09K 19/16* (2013.01); *C09K 2019/168* (2013.01); *C09K 2019/2042* (2013.01); *C09K 2019/2078* (2013.01)

(58) Field of Classification Search
CPC .... C09K 19/04; C09K 19/2007; C09K 19/16; C09K 19/586; C09K 2019/168; C09K 2019/2042; C09K 2019/2078; C09K 2019/0414; C09K 2019/0444; C09K 2019/0448; C09K 2019/528; G02F 1/13; G02F 1/1333; G02B 5/30; C07C 69/612; C07C 69/618; C07D 493/04
See application file for complete search history.

(56) References Cited

U.S. PATENT DOCUMENTS

| | | | |
|---|---|---|---|
| 2020/0071615 A1 | 3/2020 | Kodama et al. | |
| 2022/0171096 A1 | 6/2022 | Maruyama et al. | |
| 2022/0204855 A1 | 6/2022 | Kodama et al. | |
| 2023/0002679 A1* | 1/2023 | Fukushima | G02F 1/13 |

FOREIGN PATENT DOCUMENTS

| | | | | |
|---|---|---|---|---|
| CN | 101671342 A | | 3/2010 | |
| CN | 103059036 | * | 4/2013 | ............ C09K 19/58 |
| CN | 104871046 A | | 8/2015 | |
| JP | 2002-338575 A | | 11/2002 | |
| JP | 2010-90108 A | | 4/2010 | |
| JP | 2013-87109 A | | 5/2013 | |
| WO | WO2014/097895 | * | 6/2014 | ............ G02B 5/30 |
| WO | WO2018/194157 A1 | | 10/2018 | |
| WO | WO 2019/181433 A1 | * | 9/2019 | ............ C09K 19/38 |
| WO | WO2021/033634 A1 | | 2/2021 | |
| WO | WO2021/033640 A1 | | 2/2021 | |

OTHER PUBLICATIONS

International Preliminary Report on Patentability and Written Opinion of the International Searching Authority (Forms PCT/IB/326, PCT/IB/373, and PCT/ISA/237) for International Application No. PCT/JP2021/005259, dated Sep. 1, 2022, with an English translation.

(Continued)

*Primary Examiner* — Geraldina Visconti
(74) *Attorney, Agent, or Firm* — Birch, Stewart, Kolasch & Birch, LLP

(57) ABSTRACT

The present invention provides a compound having an excellent amount of change in HTP and an excellent HTP saturation rate during exposure, and a liquid crystal composition including the compound. The compound of the present invention is a compound represented by General Formula (A).

$$(Y)_n\text{-G-}(X)_m \qquad (A)$$

G represents a group represented by General Formula (B-1) or a group represented by General Formula (B-2), * represents a bonding position, and X and Y represent a predetermined group.

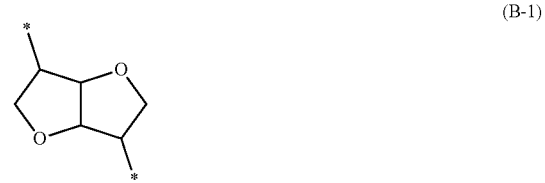

(B-1)

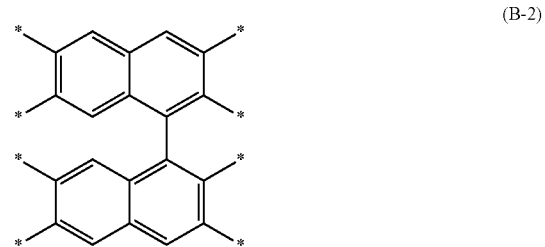

(B-2)

20 Claims, No Drawings

(56) References Cited

OTHER PUBLICATIONS

International Search Report (Form PCT/ISA/210) for International Application No. PCT/JP2021/005259, dated May 11, 2021, with an English translation.
Japanese Notice of Reasons for Refusal for corresponding Japanese Application No. 2022-501854, dated Jun. 27, 2023, with an English translation.
Chinese Office Action and Search Report for corresponding Chinese Application No. 202180015288.8, dated Dec. 30, 2023, with English translation.
Chinese Office Action for corresponding Chinese Application No. 202180015288.8, dated Mar. 30, 2024, with English translation.

\* cited by examiner

COMPOUND AND LIQUID CRYSTAL COMPOSITION

CROSS-REFERENCE TO RELATED APPLICATIONS

This application is a Continuation of PCT International Application No. PCT/JP2021/005259 filed on Feb. 12, 2021, which claims priority under 35 U.S.C. § 119(a) to Japanese Patent Application No. 2020-024935 filed on Feb. 18, 2020. Each of the above applications is hereby expressly incorporated by reference, in its entirety, into the present application.

BACKGROUND OF THE INVENTION

1. Field of the Invention

The present invention relates a compound and a liquid crystal composition.

2. Description of the Related Art

A compound exhibiting liquid crystallinity (hereinafter, also referred to as a "liquid crystalline compound") can be applied to various uses. For example, the liquid crystalline compound is applied to the manufacturing of an optically anisotropic body typified by a retardation film, or to the manufacturing of a reflective film obtained by immobilizing a cholesteric liquid crystalline phase.

Generally, the cholesteric liquid crystalline phase is formed by adding a chiral compound to a nematic liquid crystal.

For example, JP2002-338575A discloses a chiral compound having a helical twisting power (HTP) to the liquid crystalline compound. The chiral compound disclosed in JP2002-338575A has photosensitivity, and HTP changes by light irradiation.

SUMMARY OF THE INVENTION

In recent years, a photosensitive chiral compound is required to have a large amount of change in HTP. Specifically, in a case where the chiral compound is exposed to ultraviolet rays or the like, it is required that the amount of change in HTP before and after the exposure is large. Hereinafter, in the present specification, a large amount of change in HTP of a chiral compound before and after exposure is referred to as an excellent amount of change in HTP.

In addition, it is also required that a photosensitive chiral compound easily changes HTP during exposure. Specifically, it is required that the HTP changes quickly with a small amount of exposure, and the change in HTP easily reaches a saturation point. Hereinafter, in the present specification, a fact that the change in HTP of a chiral compound easily reaches a saturation point with a small amount of exposure is referred to as an excellent HTP saturation rate.

As a result of studies on characteristics of the chiral compound disclosed in JP2002-338575A, the present inventors have found that, in the chiral compound disclosed in JP2002-338575A, it is not possible to achieve both the excellent amount of change in HTP and the excellent HTP saturation rate.

Therefore, an object of the present invention is to provide a compound having an excellent amount of change in HTP and an excellent HTP saturation rate during exposure.

Another object of the present invention is to provide a liquid crystal composition including the compound.

As a result of intensive studies on the problems in the related art, the present inventors have found that the above-described objects can be accomplished by the following configurations.

(1) A compound represented by General Formula (A) described later.

(2) The compound according to (1),
in which G is the group represented by General Formula (B-1) described later.

(3) The compound according to (1) or (2),
in which Y is the group represented by General Formula (C-1) described later.

(4) The compound according to any one of (1) to (3),
in which Y represents the group represented by General Formula (C-1) described later, and
$L^1$ in the group represented by General Formula (C-1) represents a single bond.

(5) The compound according to any one of (1) to (4),
in which Y represents the group represented by General Formula (C-1) described later, and
Z in the group represented by General Formula (C-1) represents a single bond or —COO—.

(6) The compound according to any one of (1) to (5),
in which Y represents the group represented by General Formula (C-1) described later, and
$A^2$ in the group represented by General Formula (C-1) represents an aromatic group which may have a substituent.

(7) The compound according to any one of (1) to (6),
in which Y represents the group represented by General Formula (C-1) described later, and
$R^1$ in the group represented by General Formula (C-1) represents a hydrogen atom, a halogen atom, —CN, —COR, —$POR_2$, —SOR, —$SO_2R$, or —$NO_2$, and R's each independently represent a monovalent substituent.

(8) A liquid crystal composition comprising:
the compound according to any one of (1) to (7); and
a liquid crystalline compound.

According to the present invention, it is possible to provide a compound having an excellent amount of change in HTP and an excellent HTP saturation rate during exposure.

In addition, according to the present invention, it is possible to provide a liquid crystal composition including the compound.

DESCRIPTION OF THE PREFERRED EMBODIMENTS

Hereinafter, the present invention will be described in detail.

The description of the configuration requirements described below is made on the basis of representative embodiments of the present invention, but it should not be construed that the present invention is limited to those embodiments.

In the present specification, a numerical range represented using "to" means a range including numerical values described before and after the preposition "to" as a lower limit value and an upper limit value.

In addition, in the present specification, "(meth)acrylate" is a notation representing both acrylate and methacrylate.

In the present specification, in a case of simply referring to a substituent, examples of the substituent include the following substituent T.

Substituent T

Examples of the substituent T include a halogen atom (a fluorine atom, a chlorine atom, a bromine atom, an iodine atom, and the like), an alkyl group, a cycloalkyl group, an alkenyl group, a cycloalkenyl group, an alkynyl group, an aryl group, a heterocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an amino group (including an alkylamino group and an anilino group), an acylamino group, an aminocarbonylamino group, an alkoxycarbonylamino group, an aryloxycarbonylamino group, a sulfamoylamino group, an alkyl or arylsulfonylamino group, a mercapto group, an alkylthio group, an arylthio group, a heterocyclic thio group, a sulfamoyl group, a sulfo group, an alkyl or arylsulfinyl group, an alkyl or arylsulfonyl group, an acyl group, an aryloxycarbonyl group, an alkoxycarbonyl group, a carbamoyl group, an aryl or heterocyclic azo group, an imido group, a phosphino group, a phosphinyl group, a phosphinyloxy group, a phosphinylamino group, a silyl group, and a group including a polymerizable group (as a suitable specific example, a group represented by General Formula (T) and the like).

$$*-L_T-P_T \qquad \text{General Formula (T):}$$

In General Formula (T), $L_T$ represents a single bond or a divalent linking group. $P_T$ represents any of polymerizable groups represented by General Formulae (P-1) to (P-20) described below.

The divalent linking group represented by $L_T$ is not particularly limited, and an alkylene group which may include a hetero atom is preferable, an alkylene group having 1 to 10 carbon atoms, which may include an oxygen atom, is more preferable, and an alkylene group having 1 to 6 carbon atoms, which may include an oxygen atom, is still more preferable.

In General Formulae (P-1) to (P-20) shown below, * represents a bonding position. Ra represents a hydrogen atom or a methyl group. Me represents a methyl group, and Et represents an ethyl group.

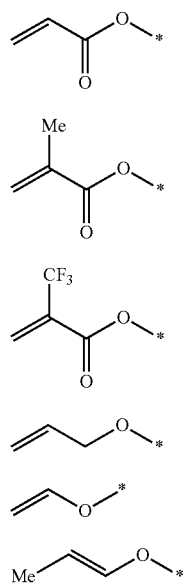

(P-1)
(P-2)
(P-3)
(P-4)
(P-5)
(P-6)

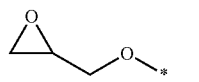
(P-7)

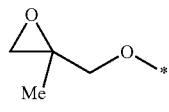
(P-8)

(P-9)

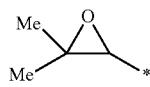
(P-10)

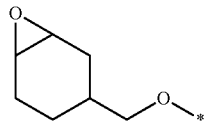
(P-11)

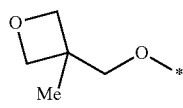
(P-12)

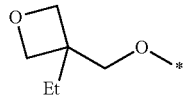
(P-13)

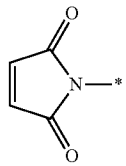
(P-14)

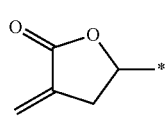
(P-15)

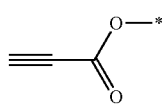
(P-16)

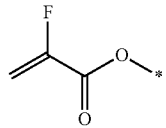
(P-17)

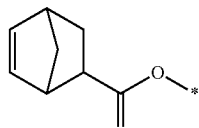
(P-18)

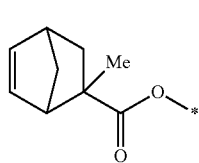
(P-19)

-continued

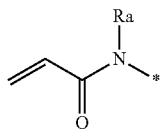
(P-20)

Among the above-described substituents, a substituent having a hydrogen atom may be further substituted with any one of the above-described substituents in the portion of the hydrogen atom in the substituent.

A bonding direction of divalent groups cited in the present specification is not limited unless otherwise specified. For example, in a compound represented by the General Formula "L-M-N", in a case where M is —OCO—C(CN)=CH—, and the position bonded to the L side is defined as *1 and the position bonded to the N side is defined as *2, M may be *1-OCO—C(CN)=CH-*2 or *1-CH=C(CN)—COO—*2. In addition, for example, in a case where M is —COO—, and the position bonded to the L side is defined as *1 and the position bonded to the N side is defined as *2, M may be *1-OCO—*2 or *1-OCO—*2.

Compound Represented by General Formula (A)

Examples of a feature point of a compound represented by General Formula (A) (hereinafter, also referred to as a "specific compound") include that a group represented by General Formula (B-1) or a group represented by General Formula (B-2) is selected as G, and a group represented by General Formula (C-1) or a group represented by General Formula (C-2) is selected as Y.

In general, in a case of being exposed to energy irradiation such as ultraviolet rays, a photosensitive chiral compound may undergo sides change due to photoisomerization so that side chains of the compound are on different sides. Since the specific compound has a group represented by G and Y, it is presumed that the structural change due to the photoisomerization is large and an excellent amount of change in HTP is achieved. In addition, since HTP changes quickly even with a small amount of exposure and the change in HTP easily reaches a saturation point, the specific compound has an excellent exposure HTP saturation rate.

Hereinafter, the specific compound will be described in detail.

$$(Y)_n\text{-G-}(X)_m \quad (A)$$

G represents a group represented by General Formula (B-1) or a group represented by General Formula (B-2).

Among these, from the viewpoint that at least one of more excellent amount of change in HTP or more excellent HTP saturation rate is obtained (hereinafter, also referred to as a "viewpoint that the effects of the present invention are more excellent"), G is preferably a group represented by General Formula (B-1). In a case where G is a group represented by General Formula (B-2), two X's may be bonded to each other to form a ring.

In the formula, * represents a bonding position.

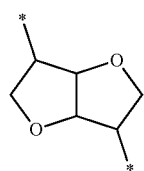
(B-1)

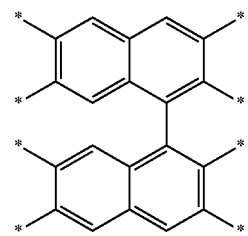
(B-2)

In a case where G is the group represented by General Formula (B-2), the specific compound is preferably a compound represented by the following formula.

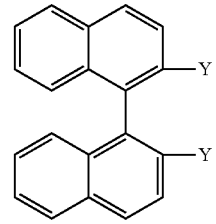

X's each independently represent a hydrogen atom or a monovalent substituent.

The monovalent substituent represented by X is not particularly limited, and examples thereof include groups exemplified by the above-described substituent T.

Among these, from the viewpoint that the effects of the present invention are more excellent, X is preferably a hydrogen atom.

Y represents a group represented by General Formula (C-1) or a group represented by General Formula (C-2).

Among these, from the viewpoint that the effects of the present invention are more excellent, Y is preferably a group represented by General Formula (C-1).

In the formula, * represents a bonding position.

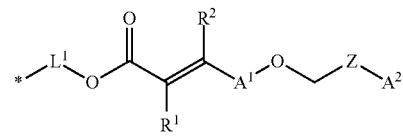
(C-1)

$L^1$ represents a single bond or a divalent linking group. Among these, from the viewpoint that the effects of the present invention are more excellent, $L^1$ is preferably a single bond.

The divalent linking group represented by $L^1$ is not particularly limited, and examples thereof include a divalent aromatic hydrocarbon group (preferably having 1 to 15 carbon atoms; examples thereof include a phenylene group, a naphthylene group, an anthracenylene group, and a biphenylene group), a divalent aliphatic hydrocarbon group (may be any of linear, branched, or cyclic; preferably having 1 to 10 carbon atoms; examples thereof include an alkylene group, an alkenylene group, and an alkynylene group), —O—, —S—, —SO$_2$—, —NR$^4$—, —CO—, —N=N—, —CH=N—, and a group of a combination of two or more these groups. $R^4$ represents a hydrogen atom or an alkyl group (preferably having 1 to 5 carbon atoms).

A hydrogen atom in the above-described divalent linking group may be further substituted with a substituent.

$R^1$ and $R^2$ each independently represent a hydrogen atom or a monovalent substituent.

The monovalent substituent represented by $R^1$ and $R^2$ is not particularly limited, and examples thereof include groups exemplified by the above-described substituent T.

Among these, from the viewpoint that the effects of the present invention are more excellent, $R^1$ is preferably a hydrogen atom, a halogen atom, —CN, —COR, —POR$_2$, —SOR, —SO$_2$R, or —NO$_2$, and more preferably a hydrogen atom or —CN.

R's each independently represent a monovalent substituent. The monovalent substituent represented by R is not particularly limited, and examples thereof include groups exemplified by the above-described substituent T.

In addition, from the viewpoint that the effects of the present invention are more excellent, $R^2$ is preferably a hydrogen atom.

$A^1$ represents an aromatic group which may have a substituent. The aromatic group represented by $A^1$ corresponds to a divalent aromatic group.

Examples of the aromatic group represented by $A^1$ include an aromatic hydrocarbon ring group and an aromatic heterocyclic group.

An aromatic ring constituting the aromatic group represented by $A^1$ may have a monocyclic structure or a polycyclic structure.

The substituent which may be included in the aromatic group represented by $A^1$ is not particularly limited, and examples thereof include groups exemplified by the above-described substituent T.

Examples of the aromatic group represented by $A^1$ include a phenylene group, a naphthylene group, a fluorenylene group, an anthracenylene group, and a biphenylene group.

Among these, from the viewpoint that the effects of the present invention are more excellent, $A^1$ is preferably an arylene group which may have a substituent, more preferably an unsubstituted arylene group, and still more preferably a phenylene group or a naphthylene group.

Z represents —(CH$_2$)$_4$— in which —CH$_2$— may be substituted with —CO— or —O—, a single bond, —(CH$_2$)$_2$—, —COO—, or —CH$_2$O—.

Among these, from the viewpoint that the effects of the present invention are more excellent, Z is preferably a single bond or —COO—, and more preferably a single bond.

$A^2$ represents an aromatic group which may have a substituent or an alicyclic group which may have a substituent. The aromatic group represented by $A^2$ corresponds to a monovalent aromatic group. The alicyclic group represented by $A^2$ corresponds to a monovalent alicyclic group.

Examples of the aromatic group represented by $A^2$ include an aromatic hydrocarbon ring group and an aromatic heterocyclic group.

An aromatic ring constituting the aromatic group represented by $A^2$ may have a monocyclic structure or a polycyclic structure.

The substituent which may be included in the aromatic group represented by $A^2$ is not particularly limited, and examples thereof include groups exemplified by the above-described substituent T.

Among these, from the viewpoint that the effects of the present invention are more excellent, the substituent which may be included in the aromatic group represented by $A^2$ is preferably an alkoxy group, an alkoxycarbonyl group, a cyano group, a hydroxyl group, a nitro group, or a carboxyl group, and more preferably an alkoxy group or an alkoxycarbonyl group.

An alicyclic ring constituting the above-described alicyclic group may have a monocyclic structure or a polycyclic structure.

The number of carbon atoms in the alicyclic group represented by $A^2$ is not particularly limited, but from the viewpoint that the effects of the present invention are more excellent, 3 to 10 is preferable.

The substituent which may be included in the alicyclic group represented by $A^2$ is not particularly limited, and examples thereof include groups exemplified by the above-described substituent T.

The alicyclic group represented by $A^2$ is not particularly limited, and examples thereof include cycloalkyl groups such as a cyclohexyl group, a norbornyl group, a tricyclodecanyl group, a tetracyclodecanyl group, a tetracyclododecanyl group, and an adamantyl group.

Among these, from the viewpoint that the effects of the present invention are more excellent, $A^2$ is preferably an aromatic group which may have a substituent, more preferably an aryl group which may have a substituent, and still more preferably a phenyl group which may have a substituent.

In the group represented by General Formula (C-1), * represents a bonding position.

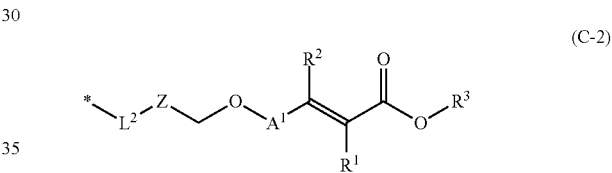

(C-2)

$R^1$, $R^2$, $A^1$, and Z in the group represented by General Formula (C-2) have the same meaning as $R^1$, $R^2$, $A^1$, and Z in General Formula (C-1), and the suitable ranges are also the same.

$L^2$ represents a single bond or -$L^3$-$A^3$-.  represents a bonding position with Z.

$L^3$ represents a single bond or a divalent linking group. The divalent linking group represented by $L^3$ is not particularly limited, and examples thereof include groups exemplified by the divalent linking group represented by $L^1$.

$A^3$ represents an aromatic group which may have a substituent or an alicyclic group which may have a substituent. The aromatic group represented by $A^3$ corresponds to a divalent aromatic group. The alicyclic group represented by $A^3$ corresponds to a divalent alicyclic group.

An aromatic ring constituting the aromatic group represented by $A^3$ may have a monocyclic structure or a polycyclic structure.

The substituent which may be included in the aromatic group represented by $A^3$ is not particularly limited, and examples thereof include groups exemplified by the above-described substituent T.

The number of carbon atoms in the alicyclic group represented by $A^3$ is not particularly limited, but from the viewpoint that the effects of the present invention are more excellent, 3 to 10 is preferable.

The substituent which may be included in the alicyclic group represented by $A^3$ is not particularly limited, and examples thereof include groups exemplified by the above-described substituent T.

Among these, from the viewpoint that the effects of the present invention are more excellent, $L^2$ is preferably a single bond.

$R^3$ represents a hydrogen atom or a monovalent substituent.

The monovalent substituent represented by $R^3$ is not particularly limited, and examples thereof include groups exemplified by the above-described substituent T.

Among these, from the viewpoint that the effects of the present invention are more excellent, $R^3$ is preferably an alkyl group which may have a substituent, an aromatic group which may have a substituent, or an alicyclic group which may have a substituent, more preferably an aromatic group which may have a substituent or an alicyclic group which may have a substituent, and still more preferably an aryl group which may have a substituent or a cycloalkyl group which may have a substituent.

In a case where G represents the group represented by General Formula (B-1), n represents 2 and m represents 0, and in a case where G represents the group represented by General Formula (B-2), n represents 2 and m represents 6.

The specific compound can be synthesized by a known method.

The specific compound may be an R-form or an S-form, or may be a mixture of R-form and S-form.

Specific examples of the specific compound are shown below, the present invention is not limited thereto.

CD-1

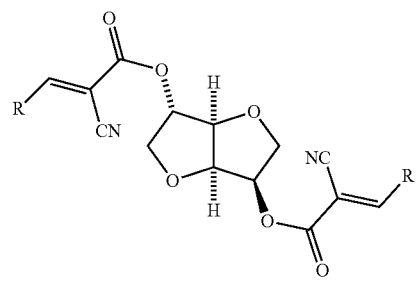

R =

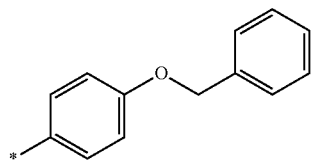 [SMILES: *c1ccc(OCc2ccccc2)cc1]

CD-2

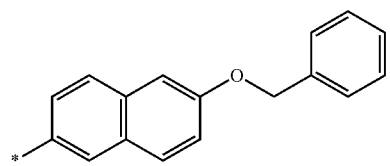 [SMILES: *c1ccc2cc(OCc3ccccc3)ccc2c1]

CD-3

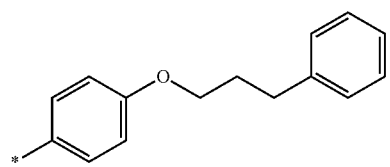 [SMILES: *c1ccc(OCCCc2ccccc2)cc1]

CD-4

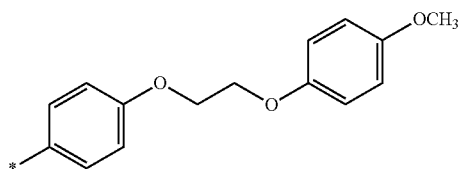 [SMILES: *c1ccc(OCCOc2ccc(OC)cc2)cc1]

CD-5

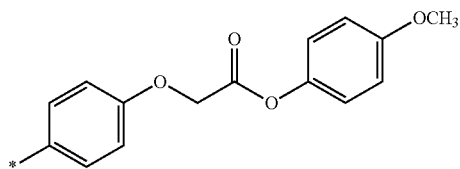 [SMILES: *c1ccc(OCC(=O)Oc2ccc(OC)cc2)cc1]

CD-6

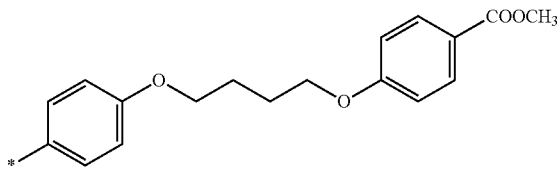 [SMILES: *c1ccc(OCCCCOc2ccc(C(=O)OC)cc2)cc1]

-continued
CD-7 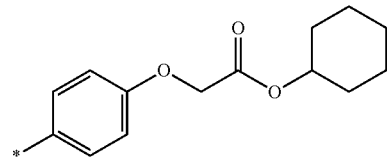 [SMILES: *c1ccc(OCC(=O)OC2CCCCC2)cc1]
CD-8 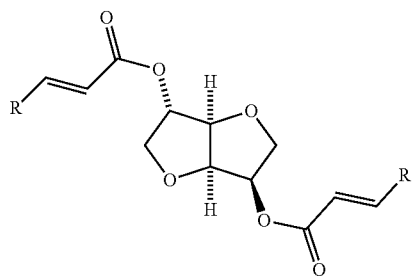 R = 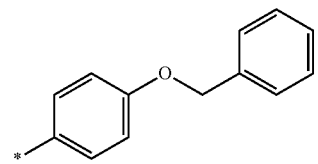 [SMILES: *c1ccc(OCc2ccccc2)cc1]
CD-9 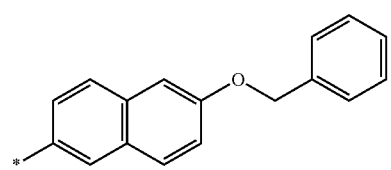 [SMILES: *c1ccc2cc(OCc3ccccc3)ccc2c1]
CD-10 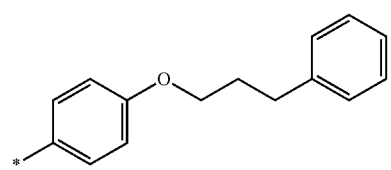 [SMILES: *c1ccc(OCCCc2ccccc2)cc1]
CD-11 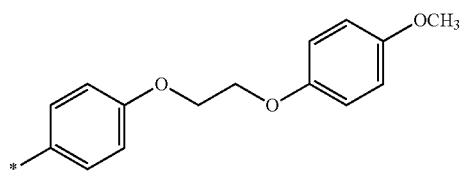 [SMILES: *c1ccc(OCCOc2ccc(OC)cc2)cc1]
CD-12 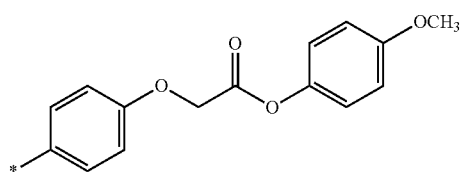 [SMILES: *c1ccc(OCC(=O)Oc2ccc(OC)cc2)cc1]
CD-13 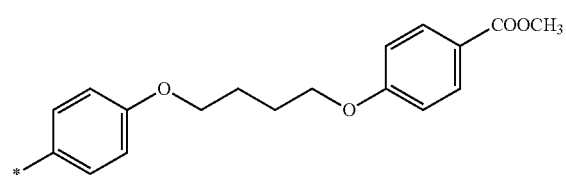 [SMILES: *c1ccc(OCCCCOc2ccc(C(=O)OC)cc2)cc1]
CD-14 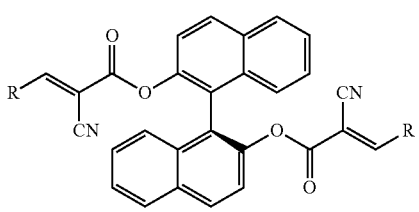 R = 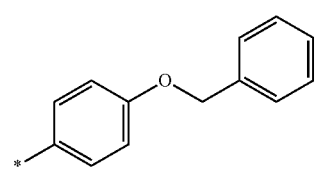 [SMILES: *c1ccc(OCc2ccccc2)cc1]

CD-15
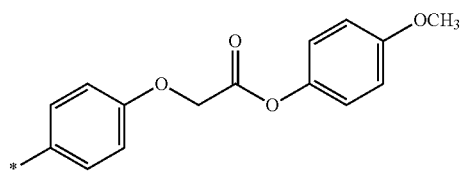 [SMILES: *c1ccc(OCC(=O)Oc2ccc(OC)cc2)cc1]
CD-16
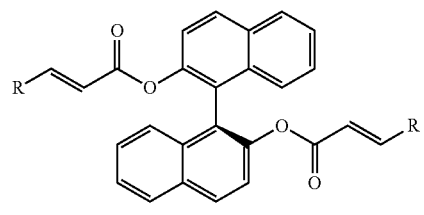
R =
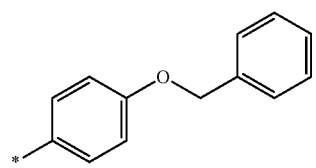 [SMILES: *c1ccc(OCc2ccccc2)cc1]
CD-17
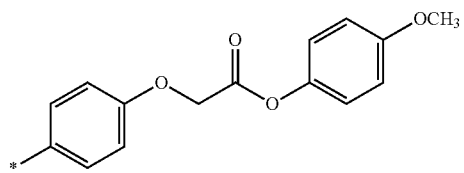 [SMILES: *c1ccc(OCC(=O)Oc2ccc(OC)cc2)cc1]
CD-18
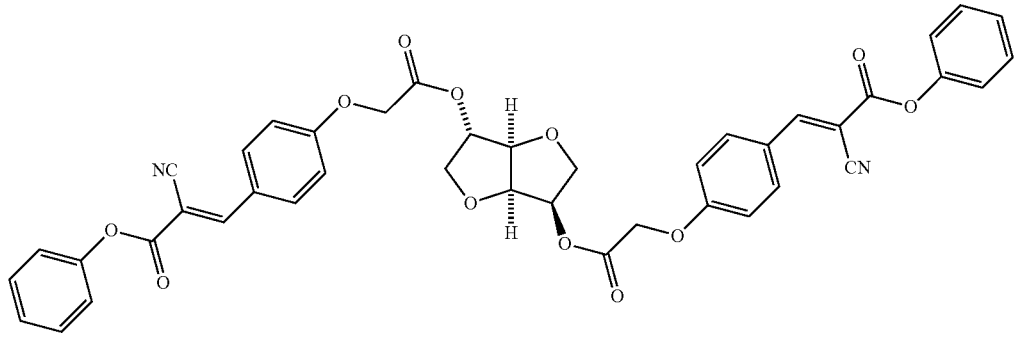 [SMILES: N#C/C(=C\c1ccc(OCC(=O)O[C@H]2CO[C@H]3[C@@H]2OC[C@H]3OC(=O)COc2ccc(/C=C(\C#N)C(=O)Oc3ccccc3)cc2)cc1)C(=O)Oc1ccccc1]
CD-19
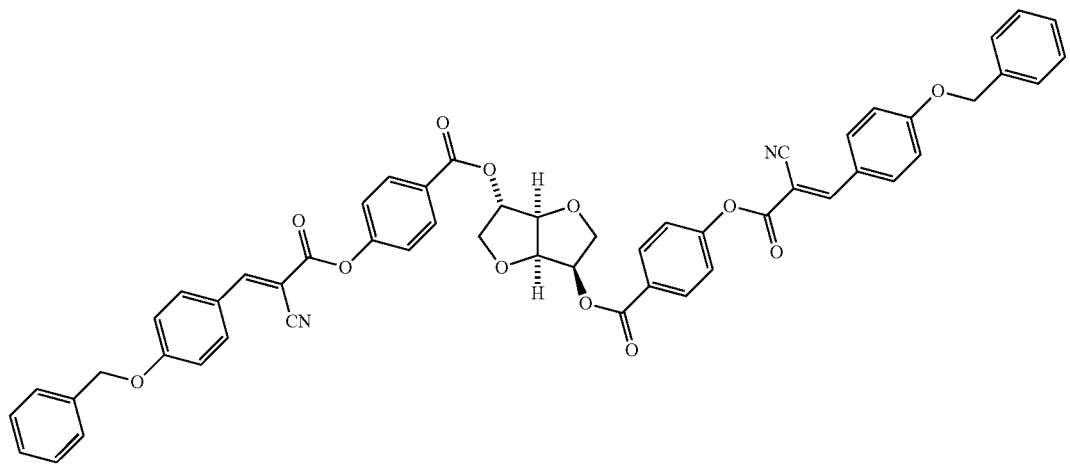 [SMILES: N#C/C(=C\c1ccc(OCc2ccccc2)cc1)C(=O)Oc1ccc(C(=O)O[C@H]2CO[C@H]3[C@@H]2OC[C@H]3OC(=O)c2ccc(OC(=O)/C(C#N)=C/c3ccc(OCc4ccccc4)cc3)cc2)cc1]

-continued
| | | |
|---|---|---|
| CD-20 | 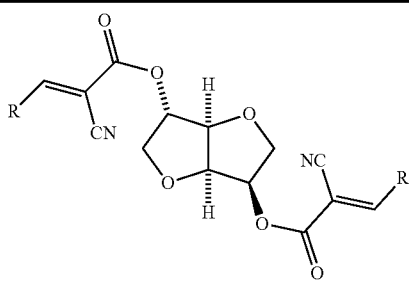 | R = 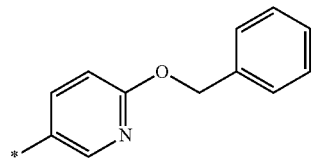 |
| CD-21 | | 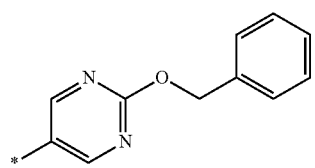 [SMILES: *c1cnc(OCc2ccccc2)nc1] |
| CD-22 | | 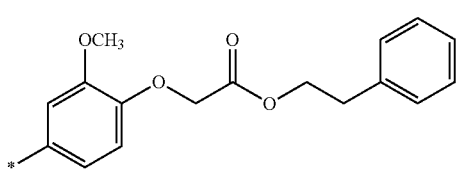 [SMILES: *c1ccc(OCC(=O)OCCc2ccccc2)c(OC)c1] |
| CD-23 | | 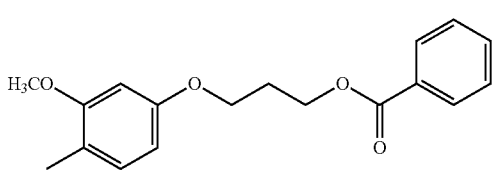 |
| CD-24 | | 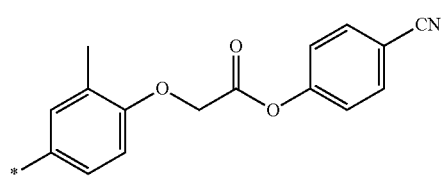 [SMILES: *c1ccc(OCC(=O)Oc2ccc(C#N)cc2)c(C)c1] |
| CD-25 | | 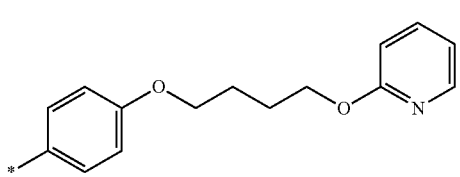 [SMILES: *c1ccc(OCCCCOc2ccccn2)cc1] |
| CD-26 | | 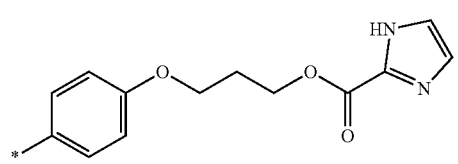 [SMILES: *c1ccc(OCCCOC(=O)c2ncc[nH]2)cc1] |
| CD-27 | 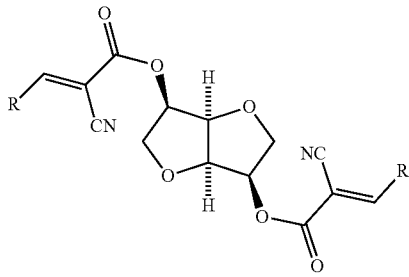 | R = 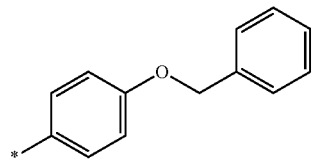 [SMILES: *c1ccc(OCc2ccccc2)cc1] |

| | |
|---|---|
| CD-28 | 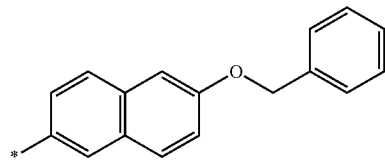 [SMILES: *c1ccc2cc(OCc3ccccc3)ccc2c1] |
| CD-29 | 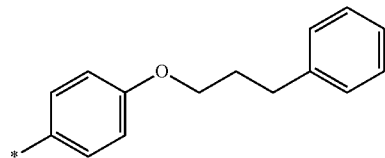 [SMILES: *c1ccc(OCCCc2ccccc2)cc1] |
| CD-30 | 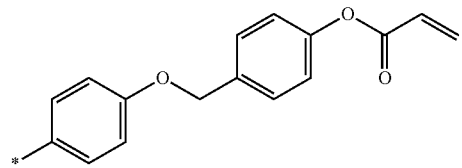 [SMILES: *c1ccc(OCc2ccc(OC(=O)C=C)cc2)cc1] |
| CD-30 | 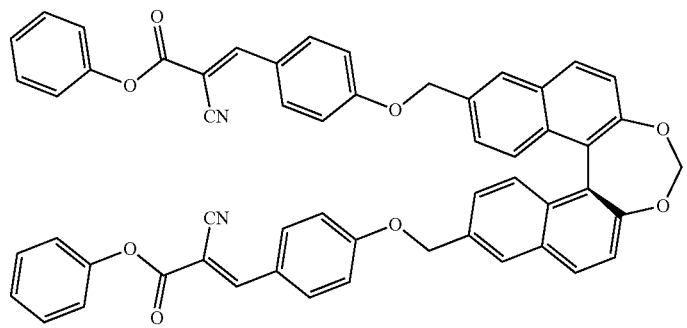 |
| CD-31 | 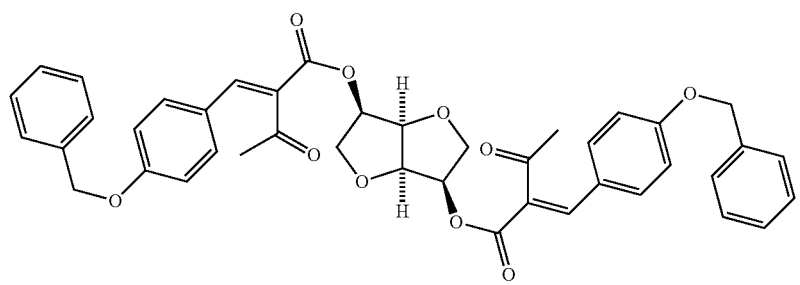 [SMILES: CC(=O)/C(=C\c1ccc(OCc2ccccc2)cc1)C(=O)O[C@@H]1CO[C@H]2[C@@H]1OC[C@H]2OC(=O)/C(=C/c1ccc(OCc2ccccc2)cc1)C(C)=O] |
| CD-32 | 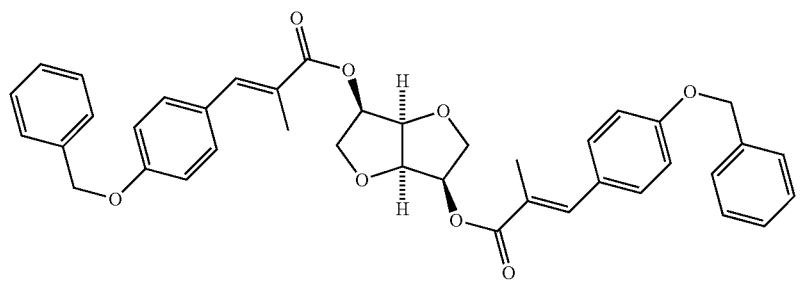 [SMILES: C/C(=C\c1ccc(OCc2ccccc2)cc1)C(=O)O[C@@H]1CO[C@H]2[C@@H]1OC[C@H]2OC(=O)/C(C)=C/c1ccc(OCc2ccccc2)cc1] |

The specific compound can be applied to various uses and is suitably used as a so-called chiral compound. For example, by using a liquid crystal composition obtained by mixing the specific compound and a liquid crystalline compound, a cholesteric liquid crystalline phase can be formed.

Hereinafter, the liquid crystal composition according to the embodiment of the present invention (hereinafter, also referred to as a "specific liquid crystal composition") will be described in detail.

Liquid Crystal Composition

The specific liquid crystal composition includes the specific compound and a liquid crystalline compound.

Hereinafter, various components essential or optionally contained in the specific liquid crystal composition will be described.

Specific Compound

The specific liquid crystal composition includes a specific compound. The specific compound is as described above.

The content of the specific compound in the specific liquid crystal composition is not particularly limited, but is preferably 0.1% to 20% by mass, more preferably 0.5% to 15% by mass, and still more preferably 1.0% to 10% by mass with respect to the total mass of the liquid crystalline compound in the specific liquid crystal composition.

In the specific liquid crystal composition, the specific compound may be used alone or in combination of two or more kinds thereof. In a case where two or more kinds thereof are used, it is preferable that the total content thereof is within the above-described range.

Liquid Crystalline Compound

The specific liquid crystal composition includes a liquid crystalline compound. The liquid crystalline compound is a compound other than the specific compound, and means a compound exhibiting liquid crystallinity.

In addition, the "compound exhibiting liquid crystallinity" is intended that the compound has properties of expressing a mesophase between a crystalline phase (low temperature side) and an isotropic phase (high temperature side) in a case of changing a temperature. As a specific observation method, optical anisotropy and fluidity derived from a liquid crystalline phase can be confirmed by performing an observation using a polarization microscope while heating the compound or lowering a temperature of the compound with a hot stage system FP90, manufactured by METTLER TOLEDO, or the like.

The liquid crystalline compound is not particularly limited as long as it has liquid crystallinity, and examples thereof include a rod-like nematic liquid crystalline compound.

Examples of the rod-like nematic liquid crystalline compound include azomethines, azoxys, cyanobiphenyls, cyanophenyl esters, benzoic acid esters, cyclohexanecarboxylic acid phenyl esters, cyanophenylcyclohexanes, cyano-substituted phenylpyrimidines, alkoxy-substituted phenylpyrimidines, phenyldioxanes, tolans, and alkenylcyclohexylbenzonitriles. High-molecular-weight liquid crystalline compounds can also be used as well as low-molecular-weight liquid crystalline compounds.

The liquid crystalline compound may be polymerizable or non-polymerizable, but is preferably polymerizable.

From the viewpoint that the cholesteric liquid crystalline phase can be immobilized, as the liquid crystalline compound, a liquid crystalline compound having one or more polymerizable groups is preferable, a liquid crystalline compound having two or more polymerizable groups is more preferable, and a liquid crystalline compound having two polymerizable groups is still more preferable.

Rod-like liquid crystalline compounds having no polymerizable group are described in various documents (for example, Y. Goto et al., Mol. Cryst. Liq. Cryst. 1995, Vol. 260, pp. 23 to 28).

Meanwhile, a polymerizable rod-like liquid crystalline compound is obtained by introducing a polymerizable group into the rod-like liquid crystalline compound. Examples of the polymerizable group include an unsaturated polymerizable group, an epoxy group, and an aziridinyl group. Among these, an unsaturated polymerizable group is preferable and an ethylenically unsaturated polymerizable group is more preferable. The polymerizable group can be introduced into the molecule of the rod-like liquid crystalline compound by various methods. The number of polymerizable groups included in the polymerizable rod-like liquid crystalline compound is preferably 1 to 6, more preferably 1 to 3, and still more preferably 2. Two or more kinds of polymerizable rod-like liquid crystalline compounds may be used in combination. In a case of using two or more kinds of polymerizable rod-like liquid crystalline compounds in combination, the alignment temperature can be lowered.

The liquid crystalline compound is preferably a compound represented by General Formula (LC).

(LC)

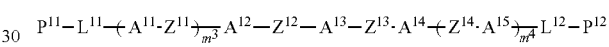

In General Formula (LC), $P^{11}$ and $P^{12}$ each independently represent a hydrogen atom or a polymerizable group. However, at least one of $P^{11}$ or $P^{12}$ represents a polymerizable group. $L^{11}$ and $L^{12}$ each independently represent a single bond or a divalent linking group. $A^{11}$ to $A^{15}$ each independently represent an aromatic hydrocarbon ring group which may have a substituent or an aromatic heterocyclic group which may have a substituent. $Z^{11}$ to $Z^{14}$ each independently represent a single bond or a divalent linking group. $m^3$ and $m^4$ each independently represent an integer of 0 or 1.

In General Formula (LC), the polymerizable group represented by $P^{11}$ and $P^{12}$ is not particularly limited, and examples thereof include the polymerizable group represented by General Formulae (P-1) to (P-20) described above. In a case where the polymerizable group represented by $P^{11}$ and $P^{12}$ represents General Formulae (P-1) to (P-20) described above, * in General Formulae (P-1) to (P-20) represents a bonding position to $L^{11}$ or $L^{12}$.

It is preferable that at least any one of $P^{11}$ or $P^{12}$ represents a polymerizable group, and it is more preferable that both $P^{11}$ and $P^{12}$ represent a polymerizable group.

In General Formula (LC), the divalent linking group represented by $L^{11}$ and $L^{12}$ is not particularly limited, and examples thereof include a linear or branched alkylene group having 1 to 20 carbon atoms, and a linking group selected from the group consisting of a linear or branched alkylene group having 1 to 20 carbon atoms, in which one or two or more —$CH_2$— is replaced with —O—, —S—, —NH—, —N($CH_3$)—, —CO—, or —COO—. As the divalent linking group represented by $L^{11}$ and $L^{12}$, a group of a linear or branched alkylene group having 1 to 20 carbon atoms, in which one or two or more —$CH_2$— is replaced with —O— is preferable.

In General Formula (LC), $A^{11}$ to $A^{15}$ each independently represent an aromatic hydrocarbon ring group which may have a substituent or an aromatic heterocyclic group which may have a substituent.

The number of ring members in the above-described aromatic hydrocarbon ring group is preferably 5 to 10.

The aromatic hydrocarbon ring constituting the aromatic hydrocarbon ring group may have a monocyclic structure or a polycyclic structure.

The number of carbon atoms in the above-described aromatic hydrocarbon ring is preferably 6 to 18 and more preferably 6 to 10. The aromatic hydrocarbon ring is not particularly limited, and examples thereof include a benzene ring, a biphenyl ring, a naphthalene ring, an anthracene ring, a phenanthrene ring, and a fluorene ring. Among these, a benzene ring is preferable as the aromatic hydrocarbon ring. The aromatic hydrocarbon ring group is composed of a structure in which two hydrogen atoms are removed on a ring of the above-described aromatic hydrocarbon ring.

The number of ring members in the above-described aromatic heterocyclic group is preferably 5 to 10.

The aromatic heterocyclic ring constituting the aromatic heterocyclic group may have a monocyclic structure or a polycyclic structure.

A hetero atom included in the above-described aromatic heterocyclic group is not particularly limited, and examples thereof include a nitrogen atom, an oxygen atom, and a sulfur atom. The number of carbon atoms in the above-described aromatic heterocyclic ring is preferably 5 to 18.

The above-described aromatic heterocyclic ring is not particularly limited, and examples thereof include a pyridine ring, a pyridazine ring, a pyrimidine ring, a pyrazine ring, a triazine ring, a thiophene ring, a thiazole ring, and an imidazole ring. The aromatic heterocyclic group is composed of a structure in which two hydrogen atoms are removed on a ring of the above-described aromatic heterocyclic ring.

The aromatic hydrocarbon ring group and aromatic heterocyclic group may have a substituent. The type of the substituent is not particularly limited, and examples thereof include known substituents. The above-described substituent is not particularly limited, and examples thereof include a halogen atom, an alkyl group, an alkoxy group, an aryl group, a hydroxyl group, an amino group, a carboxyl group, a sulfonamide group, an N-sulfonylamide group, an acyl group, an acyloxy group, a cyano group, a nitro group, and an alkoxycarbonyl group. Each of the above-described groups may be further substituted with a substituent. For example, a hydrogen atom in the alkyl group may be replaced with a fluorine atom. In addition, the number of substituents is not particularly limited, and the aromatic hydrocarbon ring group and aromatic heterocyclic group may have one substituent or may have a plurality of substituents.

Among these, as the substituent, from the viewpoint that solubility of the compound represented by General Formula (LC) is further improved, a fluorine atom, a chlorine atom, a fluoroalkyl group, an alkoxy group, or an alkyl group is preferable, and a fluoroalkyl group, an alkoxy group, or an alkyl group is more preferable.

The number of carbon atoms in the fluoroalkyl group and alkyl group, and the number of carbon atoms in an alkyl group of the alkoxy group are not particularly limited, but are preferably 1 to 10, more preferably 1 to 5, still more preferably 1 to 3, and particularly preferably 1.

The fluoroalkyl group is a group in which at least one hydrogen atom in the alkyl group is replaced with a fluorine atom, and it is preferable that all hydrogen atoms are replaced with fluorine atoms (so-called perfluoroalkyl group is preferable).

As $A^{11}$ to $A^{15}$, an aromatic hydrocarbon ring group which may have a substituent is preferable, and a phenylene group bonded at the 1-position and the 4-position is more preferable.

In General Formula (LC), the divalent linking group represented by $Z^{11}$ to $Z^{14}$ is not particularly limited, and examples thereof include a divalent aliphatic hydrocarbon group (which may be any of linear, branched, or cyclic; a divalent aliphatic hydrocarbon group having 1 to 20 carbon atoms is preferable, and examples thereof include an alkylene group; in addition, an alkenylene group or an alkynylene group may be used), —O—, —S—, —SO$_2$—, —NR$^C$—, —CO—, —N=N—, —CH=N—, and a group of a combination of two or more these groups (examples of the group of a combination of two or more groups include —CO—NH—, —CO—S—, and —COO—). Here, $R^C$ represents a hydrogen atom or an alkyl group (preferably having 1 to 10 carbon atoms). A hydrogen atom in the above-described divalent linking group may be replaced with another substituent such as a halogen atom.

As $Z^{11}$ to $Z^{14}$, among these, —COO— or —CH=CH— is preferable.

In General Formula (LC), $m^3$ and $m^4$ each independently represent an integer of 0 or 1, preferably 0.

The compound represented by General Formula (LC) can be synthesized by a known method.

Specific examples of the above-described compound represented by General Formula (LC) are described below, but the compound is not limited thereto.

LC-1

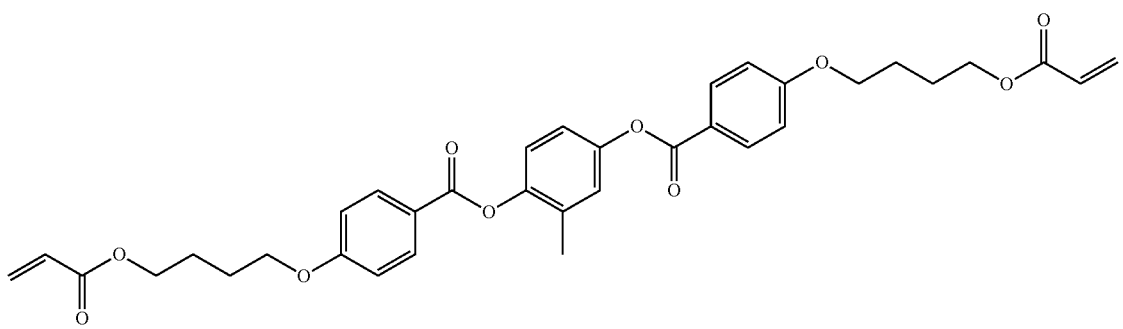

LC-2
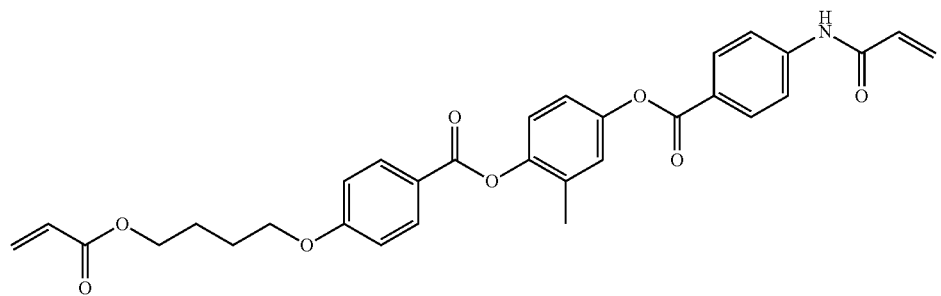
LC-3
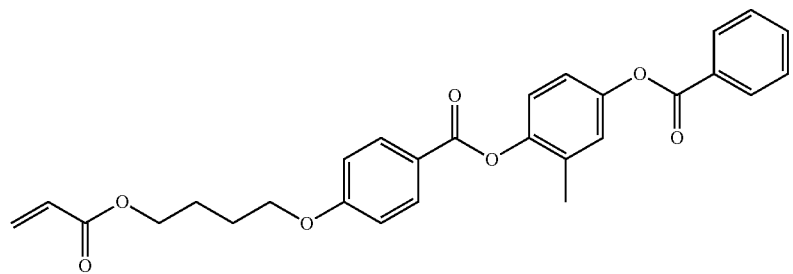
LC-4
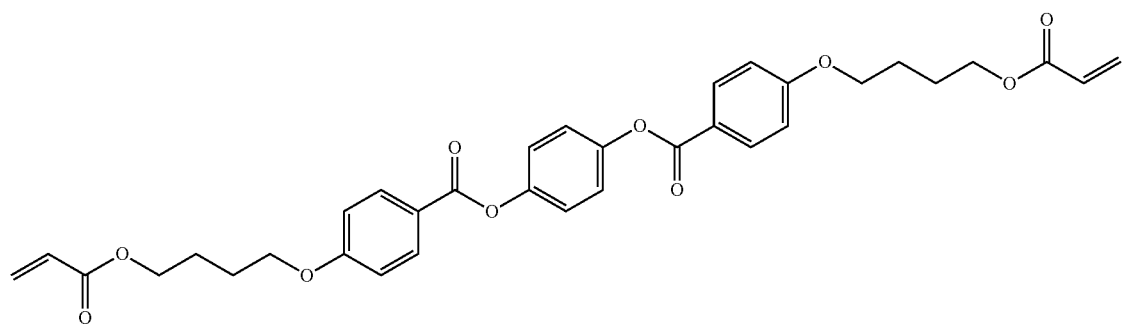
LC-5
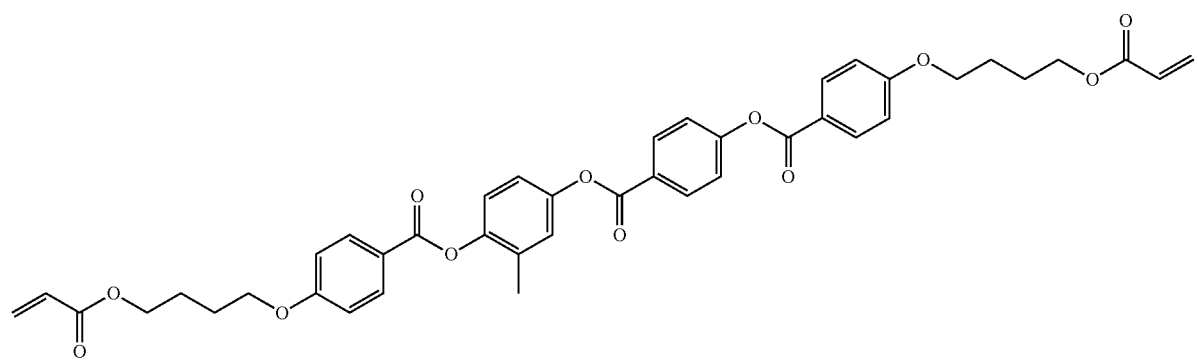

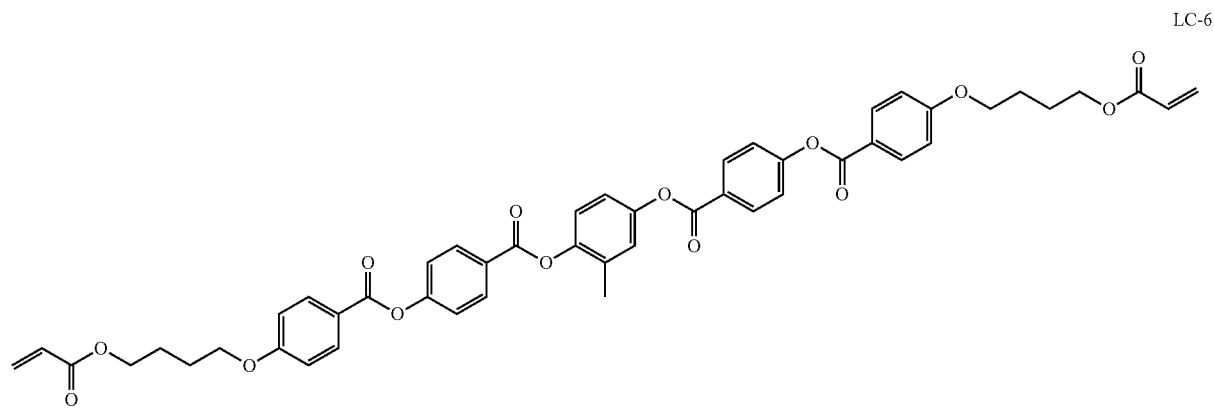
LC-6
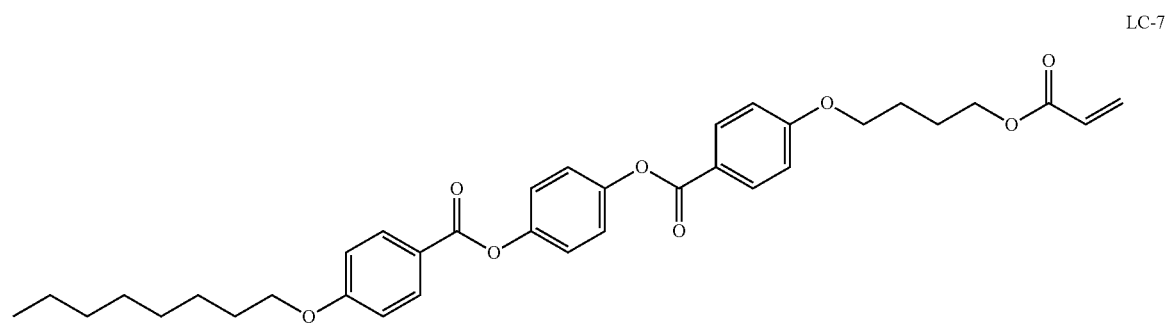
LC-7
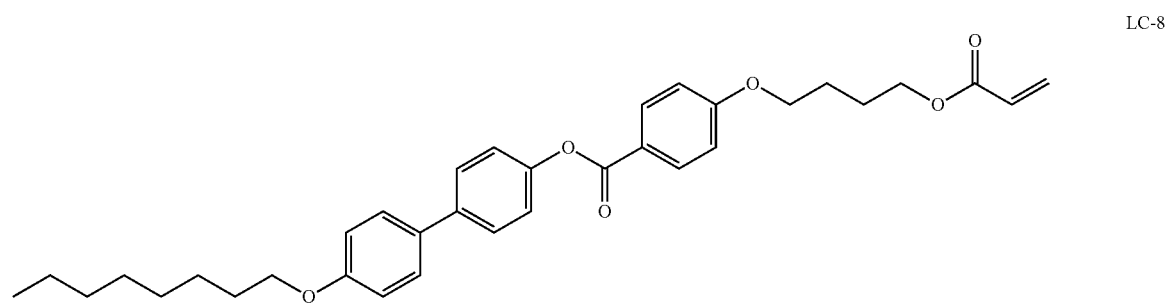
LC-8
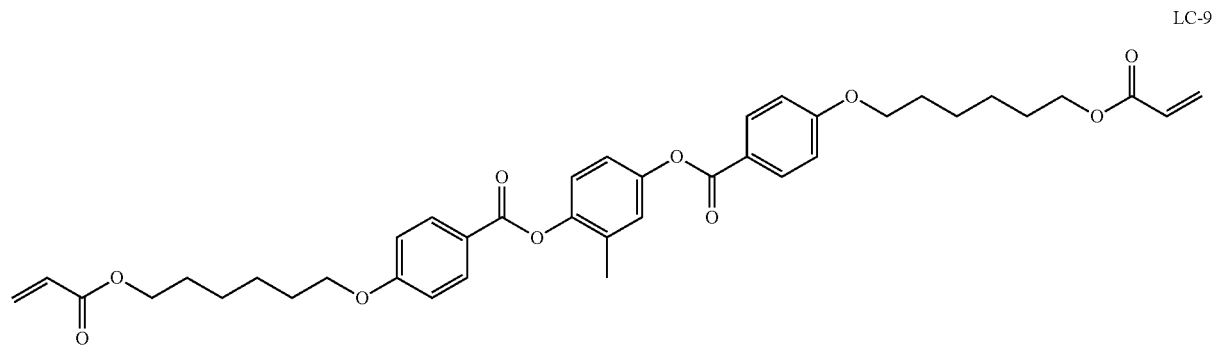
LC-9

LC-10

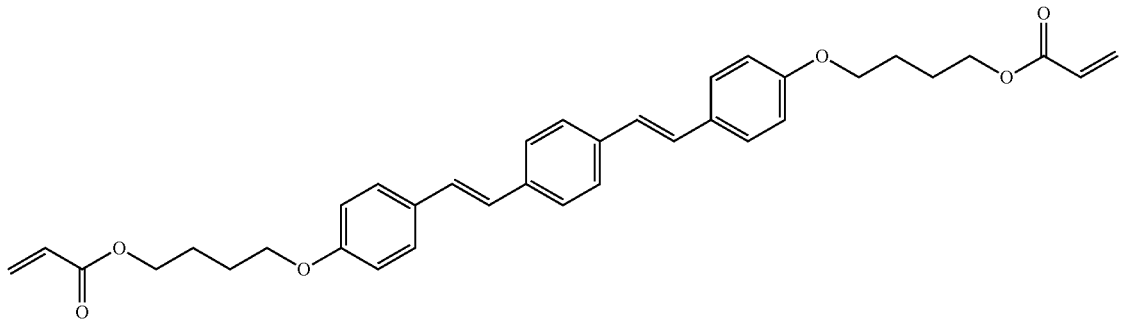

The content of the liquid crystalline compound in the specific liquid crystal composition is preferably 5% to 99% by mass, more preferably 25% to 99% by mass, and still more preferably 75% to 99% by mass with respect to the total solid content of the specific liquid crystal composition.

The solid contents mean components other than a solvent in the specific liquid crystal composition. In a case where a component is not a solvent, the component is regarded as a solid content even in a case where the property of the component is liquid.

In the specific liquid crystal composition, the liquid crystalline compound may be used alone or in combination of two or more kinds thereof. In a case where two or more kinds thereof are used, it is preferable that the total content thereof is within the above-described range.

Surfactant

The specific liquid crystal composition may include a surfactant which contributes to a stable or rapid formation of liquid crystalline phase (for example, a nematic liquid crystalline phase and a cholesteric liquid crystalline phase).

Examples of the surfactant include compounds described in paragraphs 0020 to 0031 of JP2013-047204A (JP5774518B), a fluorine-containing (meth)acrylate-based polymer, compounds represented by General Formulae (X1) to (X3) described in WO2011/162291A, and compounds represented by General Formula (I) described in paragraphs 0082 to 0090 of JP2014-119605A. At an air interface of a layer, these compounds can reduce a tilt angle of molecules of a liquid crystalline compound or can cause a liquid crystalline compound to be substantially horizontally aligned.

In the present specification, "horizontally aligned" means that a molecular axis of the liquid crystalline compound (which corresponds to a major axis of the liquid crystalline compound in a case where the liquid crystalline compound is a rod-like liquid crystalline compound) is parallel to a surface of the layer of the composition (film surface), but the molecular axis is not required to be strictly parallel thereto. In the present specification, the "horizontally aligned" means an alignment in which a tilt angle with the film surface is less than 20 degrees. In a case where the liquid crystalline compound is horizontally aligned near the air interface, alignment defects are less likely to occur, so that transparency in a visible light region is increased. On the other hand, in a case where the molecules of the liquid crystalline compound are aligned at a large tilt angle with respect to the film surface, for example, in a case of cholesteric liquid crystalline phase, since a helical axis thereof deviates from a normal line of the film surface, reflectivity may decrease, fingerprint patterns may occur, or haze may increase or diffractivity may be exhibited, which are not preferable.

Examples of the fluorine-containing (meth) acrylate-based polymer which can be used as the surfactant also include polymers described in paragraphs 0018 to 0043 of JP2007-272185A.

In a case where the specific liquid crystal composition includes a surfactant, the content of the surfactant is not particularly limited, but is preferably 0.001% to 10% by mass and more preferably 0.05% to 3% by mass with respect to the total mass of the liquid crystalline compound.

In the specific liquid crystal composition, the surfactant may be used alone or in combination of two or more kinds thereof. In a case where two or more kinds thereof are used, it is preferable that the total content thereof is within the above-described range.

Solvent

The specific liquid crystal composition may include a solvent. As the solvent, a solvent which can dissolve each component of the composition is preferable. Examples of the solvent include methyl ethyl ketone, cyclohexanone, and a mixed solvent thereof. Among these, from the viewpoint that the effects of the present invention are more excellent, the solvent is preferably methyl ethyl ketone.

In a case where the specific liquid crystal composition includes a solvent, the content of the solvent in the specific liquid crystal composition is preferably an amount at which the concentration of solid contents of the composition is 5% to 50% by mass, and more preferably an amount at which the concentration of solid contents of the composition is 10% to 40% by mass.

In the specific liquid crystal composition, the solvent may be used alone or in combination of two or more kinds thereof. In a case where two or more kinds thereof are used, it is preferable that the total content thereof is within the above-described range.

Other Components

In addition to the above-described components, the specific liquid crystal composition may also include other additives such as a polymerization initiator, an antioxidant, an ultraviolet absorber, a sensitizer, a stabilizer, a plasticizer, a chain transfer agent, a polymerization inhibitor, an anti-foaming agent, a leveling agent, a thickener, a flame retardant, a dispersant, a polymerizable monomer, and a coloring material such as a dye and a pigment.

[Polymerization Initiator]

The specific liquid crystal composition may include a polymerization initiator.

Examples of the polymerization initiator include a photopolymerization initiator and a thermal polymerization initiator.

Among these, a photopolymerization initiator capable of initiating a polymerization reaction by ultraviolet irradiation is preferable. The photopolymerization initiator is not particularly limited, and examples thereof include an alkylphenone compound, an α-carbonyl compound, acyloin ether, an α-hydrocarbon-substituted aromatic acyloin compound, a polynuclear quinone compound, a phenazine compound, and an oxadiazole compound. As the alkylphenone compound, for example, IRGACURE 907 is used.

In a case where the specific liquid crystal composition includes a polymerization initiator, the content of the polymerization initiator in the specific liquid crystal composition is not particularly limited, but is preferably 0.1% to 20% by mass and more preferably 1% to 8% by mass with respect to the total mass of the liquid crystalline compound.

In the specific liquid crystal composition, the polymerization initiator may be used alone or in combination of two or more kinds thereof. In a case where two or more kinds thereof are used, it is preferable that the total content thereof is within the above-described range.

Cured Product

In the present invention, the specific liquid crystal composition may be cured.

Curing Method and Cured Product

A method for curing (polymerizing and curing) the specific liquid crystal composition is not particularly limited, and a known method can be adopted. Examples thereof include an aspect which includes a step X of bringing a predetermined substrate into contact with the specific liquid crystal composition to form a composition layer on the substrate, a step Y of exposing the composition layer, and a step Z of subjecting the composition layer to a curing treatment.

According to this aspect, the liquid crystalline compound can be immobilized in an aligned state, and a so-called optically anisotropic body or a layer obtained by immobilizing a cholesteric liquid crystalline phase can be formed.

Hereinafter, the procedures of steps X to Z will be described in detail.

The step X is a step of bringing a substrate into contact with the specific liquid crystal composition to form a composition layer on the substrate. The substrate to be used is not particularly limited, and examples thereof include known substrates (for example, a resin substrate, a glass substrate, a ceramic substrate, a semiconductor substrate, and a metal substrate).

A method of bringing the substrate into contact with the specific liquid crystal composition is not particularly limited, and examples thereof include a method of applying the specific liquid crystal composition to the substrate and a method of immersing the substrate in the specific liquid crystal composition.

After bringing the substrate into contact with the specific liquid crystal composition, as necessary, a drying treatment may be performed in order to remove a solvent from the composition layer on the substrate. In addition, a heat treatment may be performed in order to promote the alignment of the liquid crystalline compound to be a liquid crystalline phase.

The step Y is a step of subjecting the composition layer to an exposure treatment using a wavelength of 315 nm, i-rays (wavelength: 365 nm), or the like.

In the specific compound, it is preferable that photoisomerization occurs due to the exposure treatment, so that HTP of the compound changes. In the exposure treatment, the degree of change in HTP can also be adjusted by appropriately adjusting the exposure amount, and/or the exposure wavelength and the like.

After the exposure, a heat treatment may be further performed in order to promote the alignment of the liquid crystalline compound to be a liquid crystalline phase.

The helical pitch (and thus the selective reflection wavelength and the like) of the liquid crystalline phase obtained here reflects HTP adjusted in the above-described exposure treatment.

The step Z is a step of subjecting the composition layer undergone the step Y to a curing treatment.

A method of the curing treatment is not particularly limited, and examples thereof include a photo-curing treatment and a thermal-curing treatment. Among these, a photo-curing treatment is preferable.

In a case where a photo-curing treatment is performed as the curing treatment, it is preferable that the specific liquid crystal composition includes a photopolymerization initiator. The wavelength of the light irradiated in the photo-curing treatment is preferably different from the wavelength of the light used in the above-described exposure treatment, or it is preferable that the photopolymerization initiator is not sensitive to the wavelength of the light used in the exposure treatment.

By the above-described curing treatment, a layer obtained by immobilizing the cholesteric liquid crystalline phase is formed. The layer obtained by immobilizing the cholesteric liquid crystalline phase no longer needs to exhibit liquid crystallinity anymore. More specifically, for example, as a state in which the cholesteric liquid crystalline phase is "immobilized," the most typical and preferred aspect is a state in which the alignment of the liquid crystalline compound, which is the cholesteric liquid crystalline phase, is retained. More specifically, the state is preferably a state in which the layer does not exhibit fluidity within a temperature range of usually 0° C. to 50° C., and under more severe conditions of a temperature range of −30° C. to 70° C., and in which the immobilized alignment morphology can be kept stable without being changed due to an external field or an external force.

Optically Anisotropic Body and Reflective Film

The specific liquid crystal composition can be applied to various uses. For example, using the specific liquid crystal composition, a polarizer, a reflective film (reflective layer), an antireflection film, a viewing angle compensation film, a holography, a security, a sensor, a real image projection mirror (front projection and rear projection), a virtual image projection mirror, a decorative sheet, a heat-shielding sheet, a light-shielding sheet, a screen, an optically anisotropic body, an alignment film, and the like, which are a component of an optical element, can be formed. For example, in a case where the liquid crystalline compound has a polymerizable group, a cured product can be obtained by subjecting the specific liquid crystal composition to a curing treatment (such as light irradiation treatment and heat treatment), and the cured product can be suitably applied to a polarizer, a reflective film (reflective layer), an antireflection film, a viewing angle compensation film, a holography, a security, a sensor, a real image projection mirror (front projection and rear projection), a virtual image projection mirror, a decorative sheet, a heat-shielding sheet, a light-shielding sheet, a screen, an optically anisotropic body, an alignment film, and the like, which are a component of an optical element.

The optically anisotropic body is intended to be a substance having optical anisotropy.

In addition, the reflective film corresponds to a layer obtained by immobilizing the cholesteric liquid crystalline phase, and can reflect light in a predetermined reflection band.

EXAMPLES

Hereinbelow, the present invention will be described in more detail with reference to Examples. The materials, the amounts and proportions of the materials used, the details of treatments, the procedure of treatments, and the like shown in the following Examples can be appropriately modified as long as the gist of the present invention is maintained. Accordingly, the scope of the present invention should not be construed as being limited to the following examples.

Compound Represented by General Formula (A)

The following shows an example of a method for synthesizing the specific compound. Compounds other than compounds exemplified below were synthesized with reference to the following methods.

Synthesis of Compound CD-1

A compound CD-1 shown in Table 1 was synthesized according to the following scheme.

A mixed solution including 4-benzyloxybenzaldehyde (0.942 mol, 200.0 g), cyanoacetic acid (1.131 mol, 96.18 g), pyridine (0.471 mol, 37.95 mL), aniline (0.038 mol, 3.51 g), and ethyl acetate (1000 mL) was stirred at 75° C. for 5 hours. Subsequently, methanol (400 mL) was further added to the obtained mixed solution, and then the mixed solution was cooled to room temperature. Thereafter, water (1500 mL) and a 12 N hydrochloric acid aqueous solution (42 mL) were further added to the cooled mixed solution to obtain a precipitated solid matter. After the obtained solid matter was collected by filtration, the solid matter was washed with a mixed solution of methanol and water (methanol/water=1/1 (% by volume), 500 mL), and the washed solid matter was dried by blast drying at 40° C. for 3 days to obtain an intermediate 1 (211.6 g, yield: 80.4% by mass).

Next, a mixed solution including the intermediate 1 (0.662 mol, 184.9 g), acetonitrile (887 mL), N,N-dimethylformamide (2.62 mL), and thionyl chloride (0.87 mol, 103.47 g) was stirred at 60° C. for 1 hour. Subsequently, isosorbide (0.308 mol, 45.0 g), pyridine (3.079 mol, 248 mL), and methanol (1000 mL) were sequentially added to the obtained mixed solution, and a solid matter including the target substance was precipitated. The precipitated solid matter including the target substance was collected by filtration and then washed with methanol (300 mL). The washed solid matter was purified by column chromatography to obtain the compound CD-1 (146.8 g, yield: 71.3% by mass), which was the target substance.

$^1$H-NMR of the compound CD-1 (deuterated solvent: CDCl$_3$): δ=8.19 (2H, d), 8.01 (4H, dd), 7.47 to 7.32 (10H, m), 7.07 (4H, dd), 5.37 (2H, m), 5.16 (4H, d), 5.06 (1H, t), 4.65 (1H, d), 4.22 to 4.05 (3H, m), 3.98 (1H, dd)

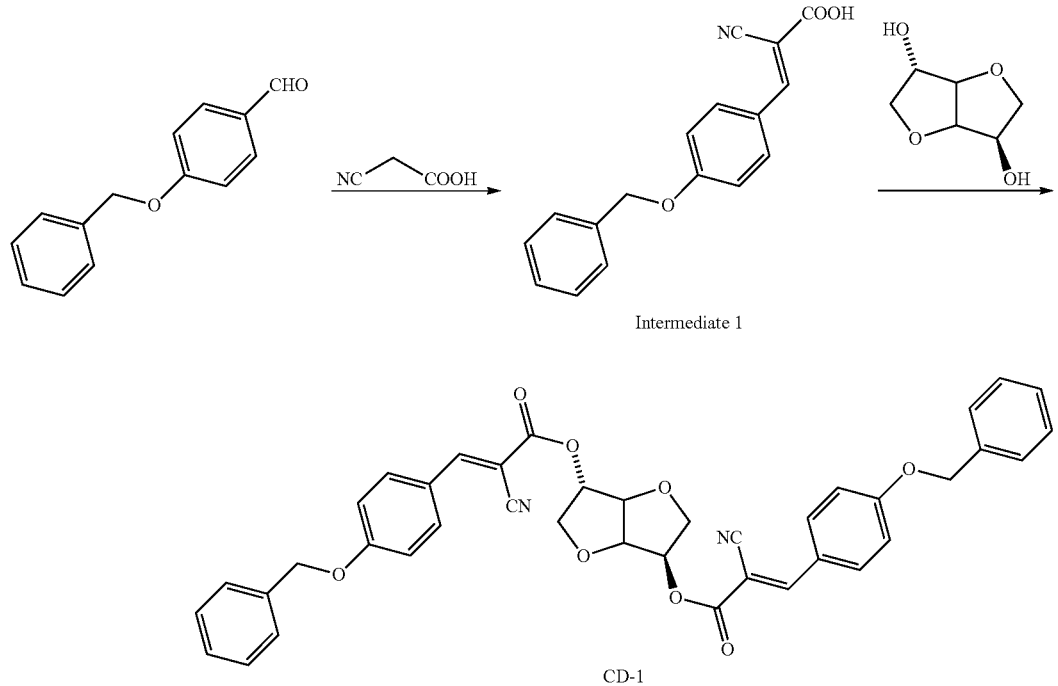

Intermediate 1

CD-1

Synthesis of Compound CD-8

A compound CD-8 shown in Table 1 was synthesized according to the following scheme.

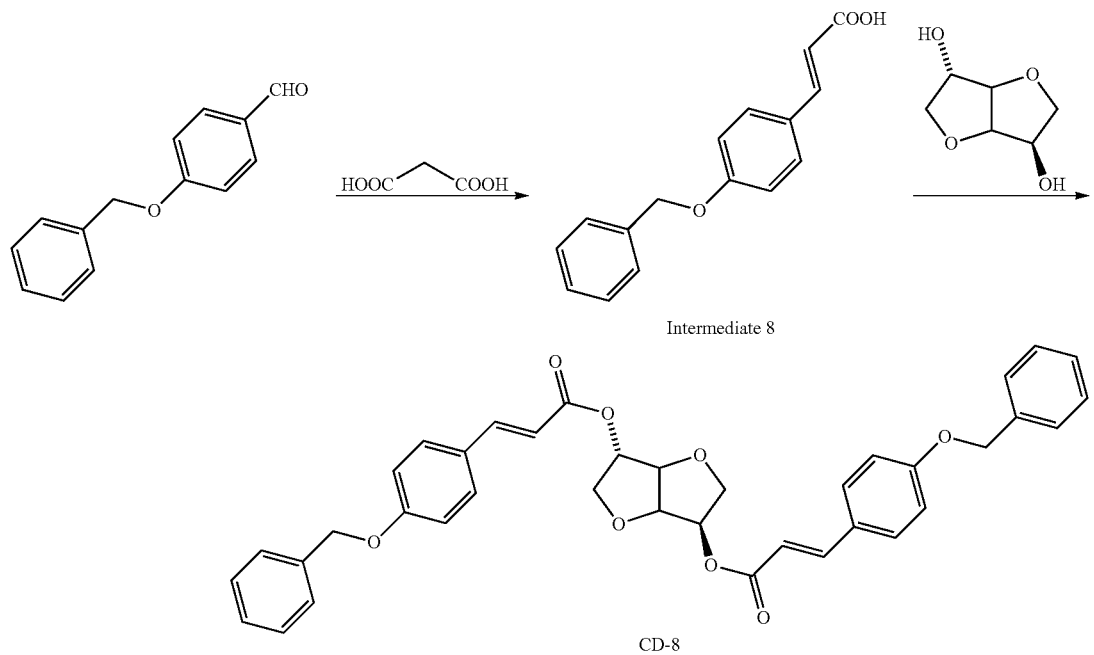

Intermediate 8

CD-8

A compound CD-8 was synthesized in the same procedure as in [Synthesis of compound CD-1], except that malonic acid was used instead of cyanoacetic acid.

Synthesis of Compound CD-14

A compound CD-14 was synthesized in the same procedure as in [Synthesis of compound CD-1], except that (R)-(+)-1,1'-bi-2-naphthol was used instead of isosorbide.

Synthesis of Compound CD-18

Using an etherification reaction and the method described in [Synthesis of compound CD-1], a compound CD-18 shown in Table 2 was synthesized according to the following scheme.

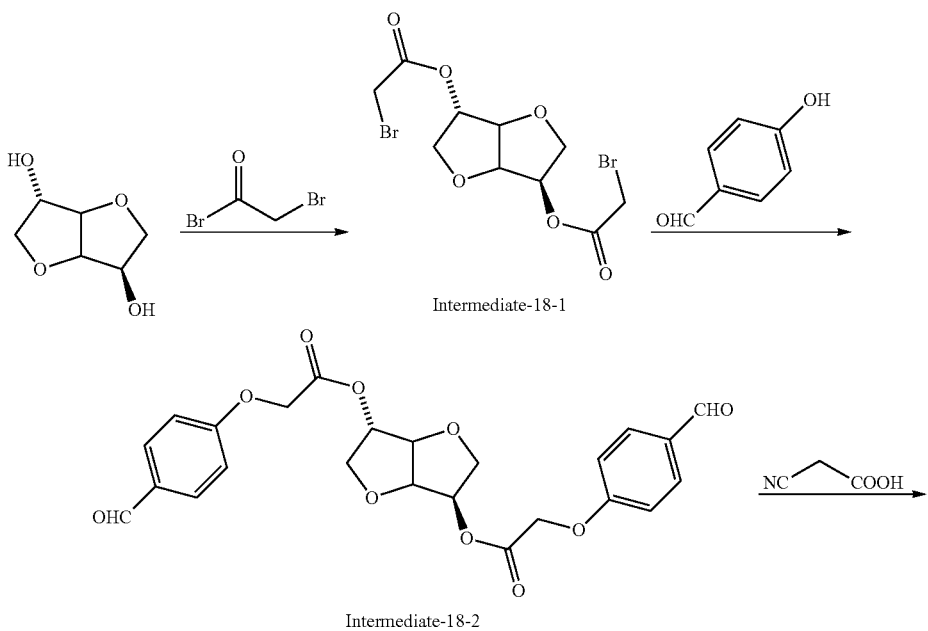

Intermediate-18-1

Intermediate-18-2

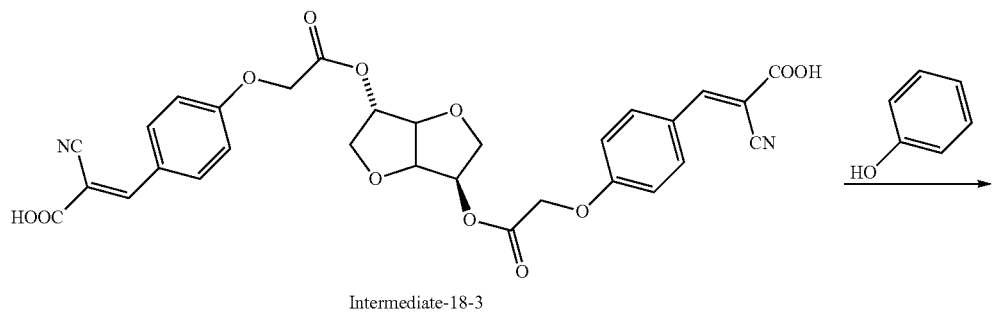
Intermediate-18-3
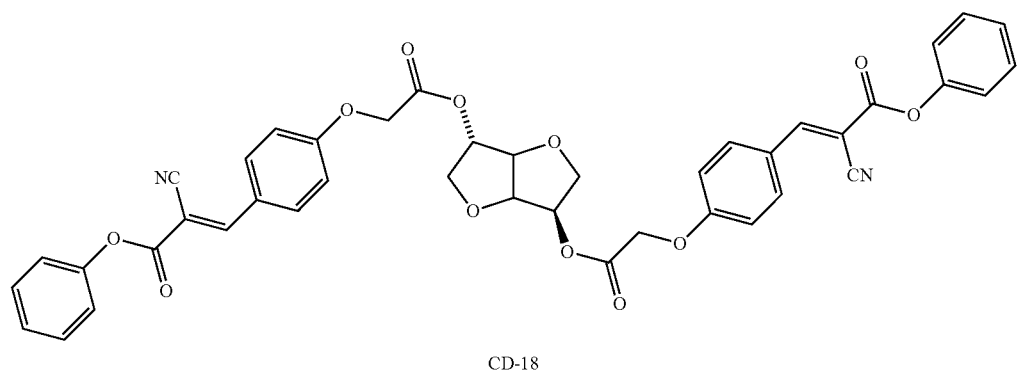
CD-18
Synthesis of Compound CD-19
Using an oxidation reaction of aldehyde and the method described in [Synthesis of compound CD-1], a compound CD-19 shown in Table 2 was synthesized according to the following scheme.
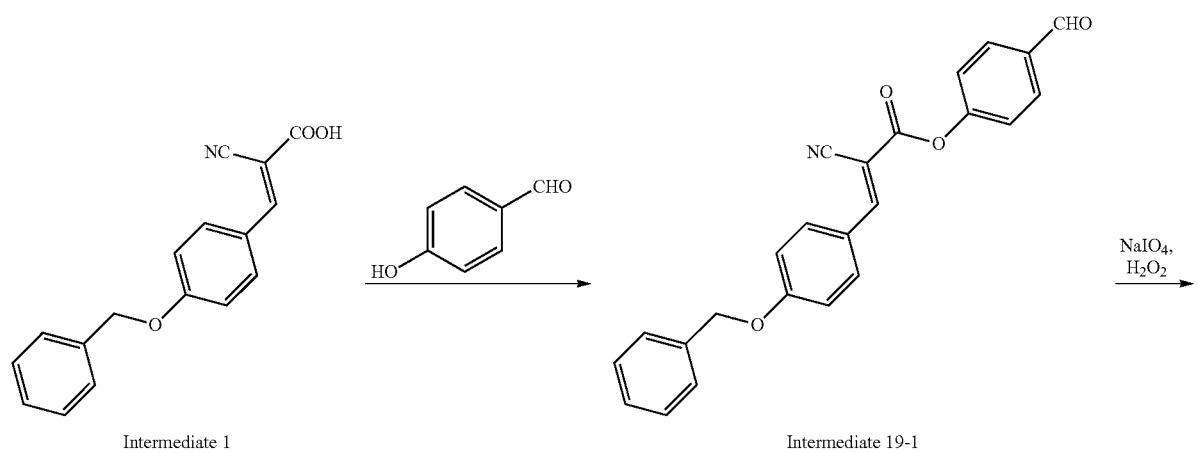
Intermediate 1                                   Intermediate 19-1

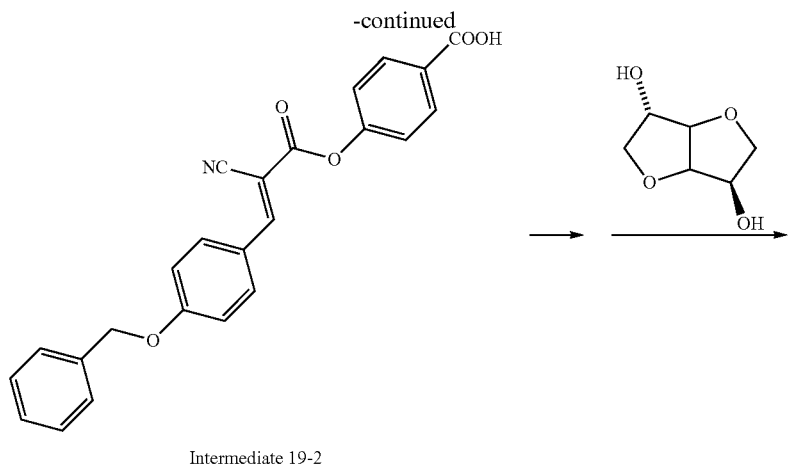

Intermediate 19-2

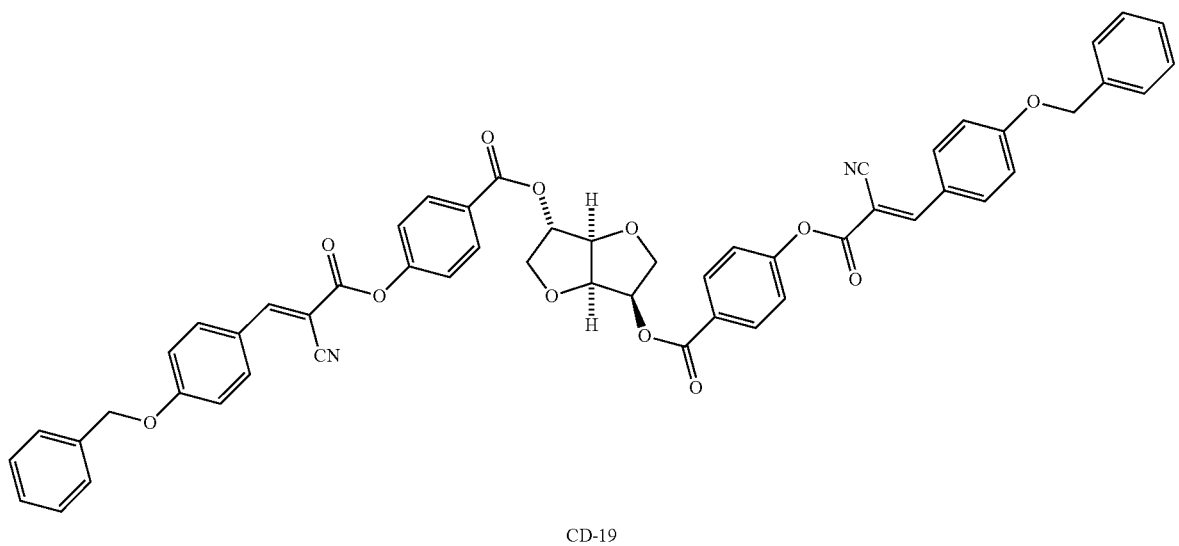

CD-19

Example 1

Preparation of Liquid Crystal Composition

A liquid crystal composition was prepared with the formulation shown below.

Liquid crystalline compound LC-1 shown below: 100 parts by mass
Compound CD-1: 1.0 part by mass
Surfactant S-1 shown below: 0.1 parts by mass
Solvent (methyl ethyl ketone (MEK)): amount at which the concentration of solid contents of the composition is 20% by mass

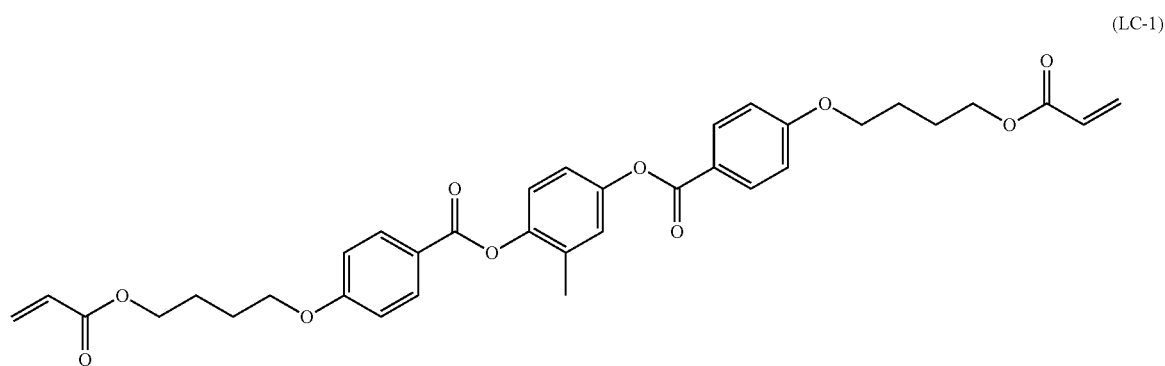 [SMILES: C=CC(=O)OCCCCOc1ccc(C(=O)Oc2ccc(OC(=O)c3ccc(OCCCCOC(=O)C=C)cc3)c(C)c2)cc1]

(LC-1)

The surfactant S-1 is a compound described in JP5774518B, and has the following structure. * represents a bonding position.

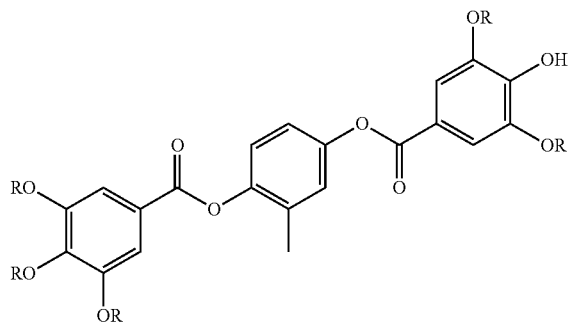

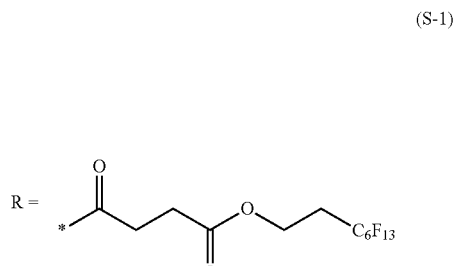

(S-1)

Production of Liquid Crystal Layer

A polyimide alignment film material SE-130 (manufactured by Nissan Chemical Corporation) was applied to a washed glass substrate to form a coating film. After firing the obtained coating film, the coating film was subjected to a rubbing treatment to produce a substrate with an alignment film.

The above-described liquid crystal composition (30 μL) was spin-coated on the rubbing-treated surface of the alignment film under the conditions of 1500 rpm and 10 seconds, and the obtained coating film was heated and dried at 90° C. for 1 minute to obtain a liquid crystal layer 1 (cholesteric liquid crystal layer) (film thickness: 1.0 μm) of Example 1.

Evaluation

<HTP Before Exposure>

With the above-described liquid crystal layer 1, using a polarization-phase difference analyzer (manufactured by Axometrics, Inc), a film thickness and twist angle of the liquid crystal layer 1 were measured. Using the obtained values, HTP before exposure was calculated according to the following expression (1).

HTP before exposure $(\mu m^{-1})$=1/{360/twist angle(°))× Film thickness (μm)×(Total addition concentration of compound CD-1 in liquid crystal layer (% by mass)/100}      Expression (1):

The obtained HTP before exposure was evaluated according to the following evaluation standard.
A: HTP before exposure was 40 $\mu m^{-1}$ or more.
B: HTP before exposure was 30 $\mu m^{-1}$ or more and less than 40 $\mu m^{-1}$.
C: HTP before exposure was less than 30 $\mu m^{-1}$.

<Amount of Change in HTP>

After further exposing the liquid crystal layer 1 to light having a wavelength of 365 nm for 1 second with an illuminance of 30 mW/cm², HTP after exposure was calculated using the expression (1). From the HTP before exposure and the obtained HTP after the 1-second exposure, an amount of change in HTP was calculated according to the following expression (2).

Amount of change in HTP $(\mu m^{-1})$=|(HTP before exposure $(\mu m^{-1})$)-(HTP after 1-second exposure $(\mu m^{-1})$)|      Expression (2):

The obtained amount of change in HTP was evaluated according to the following evaluation standard.

A: amount of change in HTP was 35 $\mu m^{-1}$ or more.
B: amount of change in HTP was 25 $\mu m^{-1}$ or more and less than 35 $\mu m^{-1}$.
C: amount of change in HTP was less than 25 $\mu m^{-1}$.

<HTP Saturation Rate>

After further exposing the liquid crystal layer 1 after being exposed for 1 second in <Amount of change in HTP> described above to light having a wavelength of 365 nm for 4 seconds with an illuminance of 30 mW/cm² (exposure for a total of 5 seconds), HTP after the 5-second exposure was calculated using the expression (1), and an HTP saturation rate was calculated according to the following expression (3).

HTP saturation rate (%)={|(HTP before exposure $(\mu m^{-1})$)-(HTP after 1-second exposure $(\mu m^{-1})$)|}/{|(HTP before exposure $(\mu^{-1})$)-(HTP after 5-second exposure $(\mu m^{-1})$)|}×100      Expression (3):

The obtained HTP saturation rate was evaluated according to the following evaluation standard.
A: HTP saturation rate was 95% or more.
B: HTP saturation rate was 90% or more and less than 95%.
C: HTP saturation rate was less than 90%.

Examples 2 to 7 and Comparative Examples 1 to 3

Liquid crystal layers 2 to 10 were produced and evaluated in the same procedure as in Example 1, except that the chiral compound shown in Table 1 was used instead of the compound CD-1.

Examples 8 to 13 and Comparative Examples 4 and 5

Liquid crystal layers 11 to 18 were produced and evaluated in the same procedure as in Example 1, except that the chiral compound shown in Table 2 was used instead of the compound CD-1, and the exposure was performed with light having a wavelength of 315 nm instead of light having a wavelength of 360 nm.

Examples 14 and 15 and Comparative Examples 6 and 7

Liquid crystal layers 19 to 22 were produced and evaluated in the same procedure as in Example 1, except that the chiral compound shown in Table 3 was used instead of the compound CD-1.

Examples 16 and 17 and Comparative Examples 8 and 9

Liquid crystal layers 23 to 26 were produced and evaluated in the same procedure as in Example 1, except that the chiral compound shown in Table 3 was used instead of the compound CD-1, and the exposure was performed with light having a wavelength of 315 nm instead of light having a wavelength of 360 nm.

Examples 18 and 19

Liquid crystal layers 27 and 28 were produced and evaluated in the same procedure as in Example 1, except that the chiral compound shown in Table 4 was used instead of the compound CD-1.

"*" in R of Tables 1 to 4 represents a bonding position.

The column of "Y" in Table 1 indicates whether Y represents the group represented by General Formula (C-1) or the group represented by General Formula (C-2).

In Tables 1 to 3, the columns of "$L^1$", "$R^1$", "Z", and "$A^2$" indicate groups corresponding to each group in General Formula (C-1).

In Table 4, the columns of "$L^1$ or $L^2$", "$R^1$", "Z", and "$A^2$ or $R^3$" indicate groups corresponding to each group in General Formula (C-1) or General Formula (C-2).

TABLE 1

| | Liquid crystal layer | | Specific compound |
|---|---|---|---|
| Example 1 | 1 | CD-1 | R = [structure] |
| Example 2 | 2 | CD-2 | [structure] |
| Example 3 | 3 | CD-3 | [structure] |
| Example 4 | 4 | CD-4 | [structure] |
| Example 5 | 5 | CD-5 | [structure] |
| Example 6 | 6 | CD-6 | [structure] |

TABLE 1-continued

| | | | |
|---|---|---|---|
| Example 7 | 7 | CD-7 | 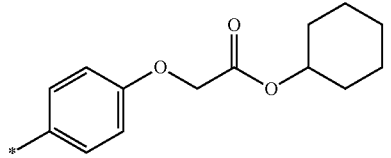 |
| Comparative Example 1 | 8 | C-1 | 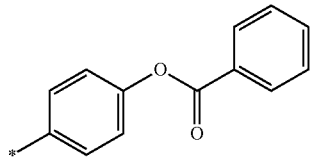 |
| Comparative Example 2 | 9 | C-2 | 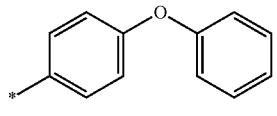 |
| Comparative Example 3 | 10 | C-3 | 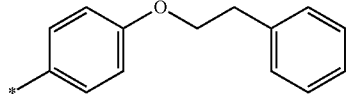 |

| | | | | | | Evaluation result | | |
|---|---|---|---|---|---|---|---|---|
| | Y | $L^1$ | $R^1$ | Z | $A^2$ | Exposure wavelength | HTP before exposure | Amount of change in HTP | HTP saturation rate |
| Example 1 | (C-1) | Single bond | CN | Single bond | Aromatic group | 365 nm | A | A | A |
| Example 2 | (C-1) | Single bond | CN | Single bond | Aromatic group | | A | A | A |
| Example 3 | (C-1) | Single bond | CN | $(CH_2)_2$ | Aromatic group | | B | B | A |
| Example 4 | (C-1) | Single bond | CN | $CH_2O$ | Aromatic group | | B | B | A |
| Example 5 | (C-1) | Single bond | CN | COO | Aromatic group | | A | A | A |
| Example 6 | (C-1) | Single bond | CN | $(CH_2)_3$—O | Aromatic group | | B | B | A |
| Example 7 | (C-1) | Single bond | CN | COO | Alicyclic group | | B | B | A |
| Comparative Example 1 | — | — | — | — | — | | A | C | C |
| Comparative Example 2 | — | — | — | — | — | | C | C | C |
| Comparative Example 3 | — | — | — | — | — | | C | C | B |

TABLE 2

| | Liquid layer crystal | Specific compound | | |
|---|---|---|---|---|
| Example 8 | 11 | CD-8 | (structure with R groups on bicyclic diol diester) | R = 4-(benzyloxy)phenyl |
| Example 9 | 12 | CD-9 | | 6-(benzyloxy)naphthalen-2-yl |
| Example 10 | 13 | CD-10 | | 4-(3-phenylpropoxy)phenyl |
| Example 11 | 14 | CD-11 | | 4-(2-(4-methoxyphenoxy)ethoxy)phenyl |
| Example 12 | 15 | CD-12 | | 4-((2-(4-methoxyphenoxy)-2-oxoethoxy))phenyl |
| Example 13 | 16 | CD-13 | | 4-(4-(4-(methoxycarbonyl)phenoxy)butoxy)phenyl |
| Comparative Example 4 | 17 | C-4 | | 4-(benzoyloxy)phenyl |
| Comparative Example 5 | 18 | C-5 | | 4-phenethoxyphenyl |

TABLE 2-continued

| | Y | L¹ | R¹ | Z | A² | Exposure wavelength | HTP before exposure | Amount of change in HTP | HTP saturation rate |
|---|---|---|---|---|---|---|---|---|---|
| Example 8 | (C-1) | Single bond | H | Single bond | Aromatic group | 315 nm | A | A | A |
| Example 9 | (C-1) | Single bond | H | Single bond | Aromatic group | | A | A | A |
| Example 10 | (C-1) | Single bond | H | (CH$_2$)$_2$ | Aromatic group | | A | A | A |
| Example 11 | (C-1) | Single bond | H | CH$_2$O | Aromatic group | | A | A | A |
| Example 12 | (C-1) | Single bond | H | COO | Aromatic group | | A | A | A |
| Example 13 | (C-1) | Single bond | H | (CH$_2$)$_3$—O | Aromatic group | | A | A | A |
| Comparative Example 4 | — | — | — | — | — | | A | C | C |
| Comparative Example 5 | — | — | — | — | — | | B | B | C |

TABLE 3

| | Liquid layer crystal | Specific compound | |
|---|---|---|---|
| Example 14 | 19 | CD-14 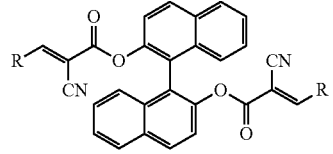 | R = 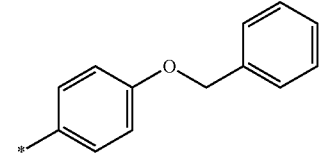 |
| Example 15 | 20 | CD-15 | 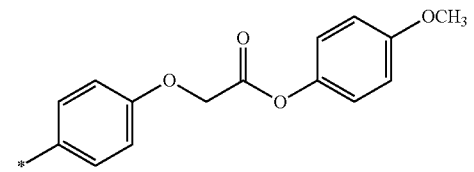 |
| Comparative Example 6 | 21 | C-6 | 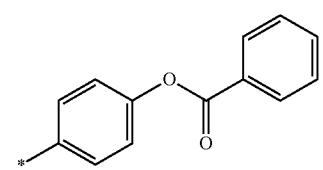 |
| Comparative Example 7 | 22 | C-7 | 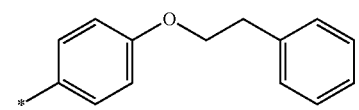 |
| Example 16 | 23 | CD-16 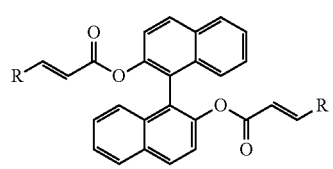 | R = 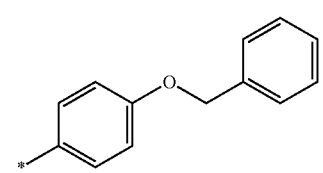 |

TABLE 3-continued

| | | | |
|---|---|---|---|
| Example 17 | 24 | CD-17 | 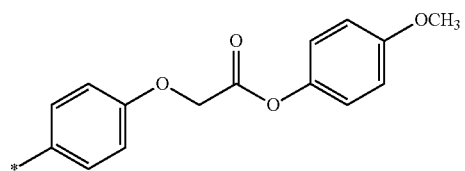 |
| Comparative Example 8 | 25 | C-8 | 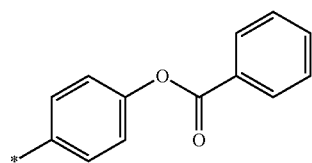 |
| Comparative Example 9 | 26 | C-9 | 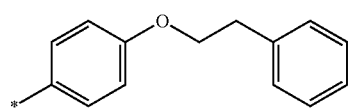 |

| | | | | | | Exposure wavelength | Evaluation result | | |
|---|---|---|---|---|---|---|---|---|---|
| | Y | $L^1$ | $R^1$ | Z | $A^2$ | | HTP before exposure | Amount of change in HTP | HTP saturation rate |
| Example 14 | (C-1) | Single bond | CN | Single bond | Aromatic group | 365 nm | B | B | B |
| Example 15 | (C-1) | Single bond | CN | COO | Aromatic group | | B | B | B |
| Comparative Example 6 | — | — | — | — | — | | A | C | C |
| Comparative Example 7 | — | — | — | — | — | | C | C | C |
| Example 16 | (C-1) | Single bond | CN | Single bond | Aromatic group | 315 nm | B | B | B |
| Example 17 | (C-1) | Single bond | CN | COO | Aromatic group | | B | B | B |
| Comparative Example 8 | — | — | — | — | — | | A | C | C |
| Comparative Example 9 | — | — | — | — | — | | C | C | C |

TABLE 4

| | Liquid crystal layer | Specific compound |
|---|---|---|
| Example 18 | 27 | CD-18 |

TABLE 4-continued

| | | | | | | | | | Evaluation result | | |
|---|---|---|---|---|---|---|---|---|---|---|---|
| Example 19 | 28 | CD-18 | | | | | | | | | |

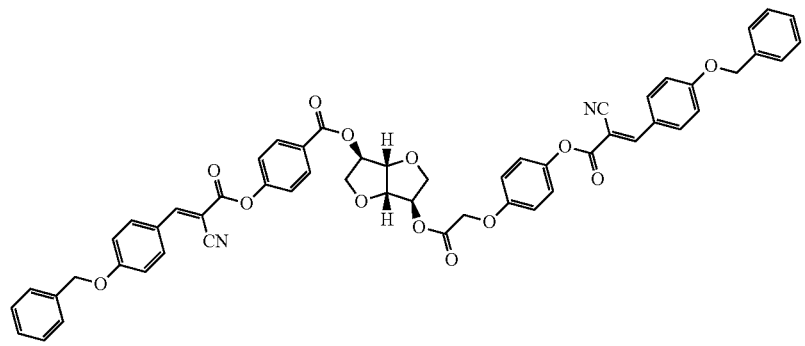 [SMILES: N#C/C(=C\c1ccc(OCc2ccccc2)cc1)C(=O)Oc1ccc(OCC(=O)O[C@@H]2CO[C@@H]3[C@H]2OC[C@H]3OC(=O)c2ccc(OC(=O)/C(C#N)=C/c3ccc(OCc4ccccc4)cc3)cc2)cc1]

| | Y | L¹ or L² | R¹ | Z | A² or R³ | Exposure wavelength | HTP before exposure | Amount of change in HTP | HTP saturation rate |
|---|---|---|---|---|---|---|---|---|---|
| Example 18 | (C-2) | Single bond | CN | COO | Aromatic group | 365 nm | B | B | B |
| Example 19 | (C-1) | —OCO—Ph | CN | Single bond | Aromatic group | | A | B | B |

From the results in Tables 1 to 4, it was confirmed that the desired effects could be obtained by using the compound according to the embodiment of the present invention.

From the comparison of Examples 1 to 6, in a case where Z in the group represented by General Formula (C-1) represents a single bond or —COO—, it was confirmed that the effects were more excellent.

From the comparison between Example 5 and Example 7, in a case where A² in the group represented by General Formula (C-1) represents an aromatic group, it was confirmed that the effects were more excellent.

From the comparison between Examples 1, 5, 8, and 12 and Examples 14 to 17, in a case where G represents the group represented by General Formula (B-1), it was confirmed that the effects were more excellent.

From the comparison between Example 1 and Example 18, in a case where Y represents the group represented by General Formula (C-1), it was confirmed that the effects were more excellent.

From the comparison between Example 1 and Example 19, in a case where L¹ represents a single bond, it was confirmed that the effects were more excellent.

What is claimed is:

1. A compound represented by General Formula (A), $$(Y)_n\text{-G-}(X)_m \quad (A)$$

G represents a group represented by General Formula (B-1) or a group represented by General Formula (B-2),
* represents a bonding position,

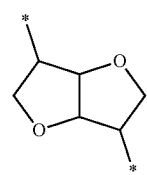

(B-1)

(B-2)

X's each independently represent a hydrogen atom or a monovalent substituent, in a case where G is a group represented by General Formula (B-2), two X's may be bonded to each other to form a ring, Y's each independently represent a group represented by General Formula (C-1) or a group represented by General Formula (C-2),

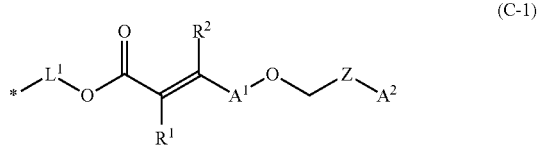

(C-1)

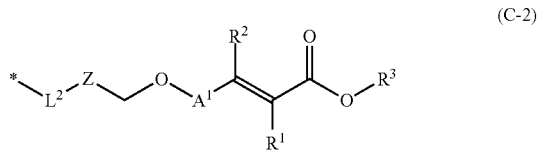

(C-2)

L¹ represents a single bond or a divalent linking group,

R¹ and R² each independently represent a hydrogen atom or a monovalent substituent, A¹ represents an aromatic group which may have a substituent, Z represents —(CH$_2$)$_4$— in which —CH$_2$— may be substituted with —CO— or —O—, a single bond, —(CH$_2$)$_2$—, —COO—, or —CH$_2$O—, A$^2$ represents an aromatic group which may have a substituent or an alicyclic group which may have a substituent, L$^2$ represents a single bond or -L$^3$-A$^3$-, L$^3$ represents a single bond or a divalent linking group, A$^3$ represents an aromatic group which may have a substituent or an alicyclic group which may have a substituent,  represents a bonding position with Z, R$^3$ represents a hydrogen atom or a monovalent substituent, in a case where G represents the group represented by General Formula (B-1), n represents 2 and m represents 0, and in a case where G represents the group represented by General Formula (B-2), n represents 2 and m represents 6, and

* represents a bonding position.

2. The compound according to claim 1,
wherein G represents the group represented by General Formula (B-1).

3. The compound according to claim 1,
wherein Y represents the group represented by General Formula (C-1).

4. The compound according to claim 1,
wherein Y represents the group represented by General Formula (C-1), and
L$^1$ in the group represented by General Formula (C-1) represents a single bond.

5. The compound according to claim 1,
wherein Y represents the group represented by General Formula (C-1), and
Z in the group represented by General Formula (C-1) represents a single bond or —COO—.

6. The compound according to claim 1,
wherein Y represents the group represented by General Formula (C-1), and
A$^2$ in the group represented by General Formula (C-1) represents an aromatic group which may have a substituent.

7. The compound according to claim 1,
wherein Y represents the group represented by General Formula (C-1), and
R$^1$ in the group represented by General Formula (C-1) represents a hydrogen atom, a halogen atom, —CN, —COR, —POR$_2$, —SOR, —SO$_2$R, or —NO$_2$, and R's each independently represent a monovalent substituent.

8. A liquid crystal composition comprising:
the compound according to claim 1; and
a liquid crystalline compound.

9. The compound according to claim 2,
wherein Y represents the group represented by General Formula (C-1).

10. The compound according to claim 2,
wherein Y represents the group represented by General Formula (C-1), and
L$^1$ in the group represented by General Formula (C-1) represents a single bond.

11. The compound according to claim 2,
wherein Y represents the group represented by General Formula (C-1), and
Z in the group represented by General Formula (C-1) represents a single bond or —COO—.

12. The compound according to claim 2,
wherein Y represents the group represented by General Formula (C-1), and
A$^2$ in the group represented by General Formula (C-1) represents an aromatic group which may have a substituent.

13. The compound according to claim 2,
wherein Y represents the group represented by General Formula (C-1), and
R$^1$ in the group represented by General Formula (C-1) represents a hydrogen atom, a halogen atom, —CN, —COR, —POR$_2$, —SOR, —SO$_2$R, or —NO$_2$, and R's each independently represent a monovalent substituent.

14. A liquid crystal composition comprising:
the compound according to claim 2; and
a liquid crystalline compound.

15. The compound according to claim 3,
wherein Y represents the group represented by General Formula (C-1), and
L$^1$ in the group represented by General Formula (C-1) represents a single bond.

16. The compound according to claim 3,
wherein Y represents the group represented by General Formula (C-1), and
Z in the group represented by General Formula (C-1) represents a single bond or —COO—.

17. The compound according to claim 3,
wherein Y represents the group represented by General Formula (C-1), and
A$^2$ in the group represented by General Formula (C-1) represents an aromatic group which may have a substituent.

18. The compound according to claim 3,
wherein Y represents the group represented by General Formula (C-1), and
R$^1$ in the group represented by General Formula (C-1) represents a hydrogen atom, a halogen atom, —CN, —COR, —POR$_2$, —SOR, —SO$_2$R, or —NO$_2$, and R's each independently represent a monovalent substituent.

19. A liquid crystal composition comprising:
the compound according to claim 3; and
a liquid crystalline compound.

20. The compound according to claim 4,
wherein Y represents the group represented by General Formula (C-1), and
Z in the group represented by General Formula (C-1) represents a single bond or —COO—.

* * * * *